(12) United States Patent
Lomonossoff et al.

(10) Patent No.: US 7,208,655 B1
(45) Date of Patent: Apr. 24, 2007

(54) MODIFIED PLANT VIRUSES AS VECTORS

(75) Inventors: George Peter Lomonossoff, Norwich (GB); John Emil Johnson, San Diego, CA (US)

(73) Assignee: The Dow Chemical Company, Midland, MI (US)

( * ) Notice: Subject to any disclaimer, the term of this patent is extended or adjusted under 35 U.S.C. 154(b) by 380 days.

(21) Appl. No.: 09/580,704

(22) Filed: May 30, 2000
(Under 37 CFR 1.47)

Related U.S. Application Data

(63) Continuation-in-part of application No. 08/137,032, filed as application No. PCT/GB92/00589 on Apr. 2, 1992, now Pat. No. 6,110,466.

(51) Int. Cl.
| | |
|---|---|
| A01H 5/00 | (2006.01) |
| C12N 15/82 | (2006.01) |
| C12N 15/83 | (2006.01) |
| A61K 48/00 | (2006.01) |
| A01H 1/00 | (2006.01) |

(52) U.S. Cl. .................................. 800/298; 435/320.1
(58) Field of Classification Search .................. 435/6, 435/235.1, 410, 468, 239, 419, 320.1, 421; 536/23.1; 424/199.1; 514/2
See application file for complete search history.

(56) References Cited

U.S. PATENT DOCUMENTS

| | | | |
|---|---|---|---|
| 4,407,956 A | 10/1983 | Howell | |
| 4,593,002 A | 6/1986 | Dulbecco | |
| 4,722,840 A | 2/1988 | Valenzuela et al. | |
| 4,885,248 A | 12/1989 | Ahlquist | |
| 4,956,282 A | 9/1990 | Goodman et al. | |
| 5,173,410 A | 12/1992 | Ahlquist | |
| 5,316,931 A * | 5/1994 | Donson et al. | 435/468 |
| 5,437,976 A * | 8/1995 | Utermohlen | 435/6 |
| 5,500,360 A | 3/1996 | Ahlquist et al. | |
| 5,846,795 A | 12/1998 | Ahlquist et al. | |
| 5,874,087 A * | 2/1999 | Lomonossoff et al. | 424/199.1 |
| 5,958,422 A * | 9/1999 | Lomonossoff | 424/199.1 |

FOREIGN PATENT DOCUMENTS

| | | |
|---|---|---|
| EP | 067 553 A2 | 12/1982 |
| EP | 0174 759 A1 | 3/1986 |
| EP | 194 809 A1 | 9/1986 |
| EP | 221 044 B1 | 5/1987 |
| EP | 0 278 667 | 8/1988 |
| WO | WO 87/06261 | 10/1987 |
| WO | WO 89/08145 | 4/1989 |
| WO | WO 90/00611 | 1/1990 |

OTHER PUBLICATIONS

Harlow and Lane Antibodies A Laboratory Manual, Cold Spring Harbor Laboratory Press, pp. 75-77, 1988.*
U.S. Appl. No. 07/600,881, Grill et al., pp. 1-88, Oct. 22, 1990.*
U.S. Appl. No. 07/600,244 Grill et al., pp. 1-88, Oct. 22, 1990.*
Brennan et al. Mol. Biotech. 2001; 17:15-26.*
Porta et al. Virology. 1994; 202:949-55.*
Takamatsu et al. FEBS letters. 1990; 269: 73-6.*
Usha et al. 1993. Virology; 197:366-74.*
Abad-Zapatero, C. et al., "Structure of southern bean mosaic virus at 2.8 Å resolution," *Nature* 286:33-39 (1980).
Abstract W47-007—Submitted to 8th International Congress to Virology in Berlin (1990) Rohl et al., Investigation of the structure and function of comovirus capsids.
Ahlquist, P., and Janda, M., "cDNA Cloning and In Vitro Transcription of the Complete Brome Mosaic Virus Genome," *Mol. Cell Biol.* 4:2876-2882 (1984).
Ahlquist et al., "Molecular Studies of Brome Mosaic Virus Using Infectious Transcripts from Cloned cDNA" *Adv. Virus. Res.* 32:215-42 (1987).
Ahlquist et al.,"Sindbis Virus Proteins nsP1 and nsP2 Contain Homology to Nonstructural Proteins from Several RNA Plant Viruses" *J. Virol.* 53(2):536-42 (1985).
Ahlquist et a., "Nucleotide Sequence of the Brome Mosaic Virus and its Implications for Viral Replication" *J. Mol. Biol.* 172:369-83 (1984).
Ahlquist et al., "Complete Nucleotide Sequence of Brome Mosaic Virus RNA3" *J. Mol. Biol.* 153:23-38 (1981).
Argos et al., "Similarity in gene organization and homology between proteins of animal picornaviruses and a plant comovirus suggest common ancestry of these virus families," *Nucleic Acids Research* 12(18):7251-7267 (1984).
Biggin, M.D. et al., "Buffer gradient gels and $^{35}$S label as an aid to rapid DNA sequence determination," *Proc. Natl. Acad. Sci. USA* 80:3963-3965 (1983).
Blimboim, H.C. and Doly, J.,"A rapid alkaline extraction procedure for screening recombinant plasmid DNA," *Nucleic Acids Res.* 7:1513-1523 (1979).
Chanh, T.C., et al., "Induction of anti-HIV neutralizing antibodies by synthetic peptides," *EMBO J.* 5:3065-3071 (1986).
Chen et al., "Capsid Structure and RNA Packaging in Comoviruses," *Seminars in Virology* 1:453-466 (1990).
Chen, Z. et al., "Protein-RNA Interactions in an Icosahedral Virus at 3.0 A Resolutions," *Science* 245:154-159 (1989).
Crabbe et al., "Modelling of poliovirus, HIV-1 antigen chimaeras," *FIBS Letters* 271:194-198 (1990).
Dalgleish, A.G., et al.,"Neutralization of Diverse HIV-1 Strains by Monoclonal Antibodies Raised against a gp41 Synthetic Peptide," *Virology* 165:209-215 (1988).
De Varennes, A. and Maule, A.J., "Independent Replication of Cowpea Mosaic Virus Bottom Component RNA:*In Vivo* Instability of the Viral RNAs," *Virology* 144:495-501 (1985).
Dessens, J.T. and Lomonossoff, G.P., "Mutational Analysis of the Putative Catalytic Triad of the Cowpea Mosaic Virus 24K Protease," *Virology* 184:738-746 (1991).

(Continued)

*Primary Examiner*—David Guzo
(74) *Attorney, Agent, or Firm*—Jarett K. Abramson

(57) ABSTRACT

The invention relates to assembled particles of a plant virus containing a predetermined foreign peptide as part of the coat protein of the virus, and a method for their production. The foreign peptide is preferably a biologically functional peptide, the biological application of which requires or is enhanced by presentation of the peptide in association with a larger molecule or particle.

4 Claims, 12 Drawing Sheets

OTHER PUBLICATIONS

Figure 1A:
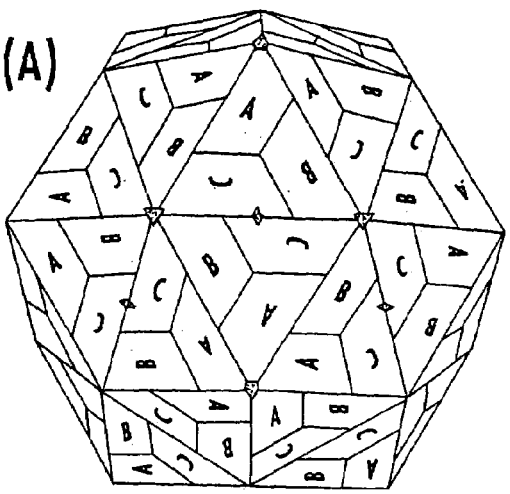

Eggen et al. "Improvements of the Infectivity of In Vitro Transcripts from Cloned Cowpea Mosaic Virus cDNA: Impact of terminal Nucleotide Sequences" *Virology* 173:447-55 (1989).

Eggen et al., "Analysis of Sequences Involved in Cowpea Mosaic Virus RNA Replication Using Site Specific Mutants" *Virology* 173:456-64 (1989).

Evans et al., "An engineered poliovirus chimaera elicits broadly reactive HIV-1 neutralizing antibodies," *Nature* 339:385-388 (1989).

Feinberg, A.P. and Vogelstein, B., "A Technique for Radiolabeling DNA Restriction Endonuclease Fragments to High Specific Activity," *Analytical Biochem.* 132:6-13 (1983).

Fox, "No winners against AIDS," *Bio/Technology* 12:128 (1994).

French et al., "Bacterial Gene Inserted in an Engineered Plant Virus: Efficient Expression in a Monocotyledenous Plant" *Science* 231:1294-97 (1986).

Goldbach, R., et al., "Independent replication and expression of B-component RNA of cowpea mosaic virus," *Nature* 286:297-300 (1980).

Gorbalenya et al., "An NTP-Binding Motif is the Most Conserved Sequence in a Highly Diverged Monophyletic Group of Proteins Involved in Positive Strand RNA Viral Replication," *J. of Mol Evol* 28:256-268 (1989).

Harrison. S.C. et al., "Tomato bushy stunt virus at 2.9 Å resolution," *Nature* 276:368-373 (1978).

Haselhoff et al., "Striking Similarities in Amino Acid Sequence Among Nonstructural Proteins Encoded by RNA Viruses that Have Similar Genomic Organization" *Proc. Natl. Acad. Sci. USA* 81:4358-62 (1984).

Hayes, R.J., et al., "Stability and expression of bacterial genes in replicating geminivirus vectors in plants," *Nucleic Acids Research* 17(7):2391-2403 (1989).

Haynes et al., "Development of a Genetically-Engineered, Canidate Polio Vaccine Employing the Self-Assembling Properties of the Tabacco Mosaic Virus Coat Protein," *Bio/Technology* 4:637-641 (1986).

Hogle, J.M. et al., "Structure and Assembly of Turnip Crinkle Virus I. X-ray Crystallographic Structure Analysis at 3.2 Å Resolution," *J. Mol. Biol.* 191:625-638 (1986).

Holness, C.L., et al., "Identifcation of the Initiation Codons for Translation of Cowpea Mosaic Virus Middle Component RNA Using Site-Directed Mutagenesis of an Infectious cDNA Clone," *Virology* 172:311-320 (1989).

Janda et al., High Efficiency T7 Polymerase Synthesis of Infectious RNA from Cloned Brome Mosaic Virus cDNA and Effect of 5' Extensions on Transcript Infectivity *Virology* 158:259-262 (1987).

Kennedy, R.C., et al., "Antiserum to a Synthetic Peptide Recognizes the HTLV-III Envelope Glycoprotein," *Science* 231:1556-1559 (1986).

Kunkel, T.A., "Rapid and efficient site-specific mutagenesis without phenotypic selection," *Proc. Nat. Acad. Sci. USA* 82:488-492 (1985).

Laemmli, U.K., "Cleavage of Structural Proteins during the Assembly of the Head of Bacteriophage T4," *Nature* 227:680-685 (1970).

Lehrach, H., et al., "RNA Molecular Weight Determinations by Gel Electrophoresis under Denaturing Conditions, a Critical Reexamnation," *Biochemistry* 16:4743-4751 (1977).

Liljas, L. et al., "Structure of Satellite Tobacco Necrosis Virus at 3.0 Å Resolution," *J. Mol. Biol.*, 159:93-108 (1982).

Lomonossoff, G.P.,et al., "The location of the first AUG codons in cowpea mosaic virus RNAs," *Nucleic Acids Research* 10:4861-4872 (1982).

Lomonossoff, G.P. and Shanks, M., "The nucleotide sequence of cowpea mosaic virus B RNA," *EMBO J.* 2: 2253-2258 (1983).

Lomonossoff et al., "The Synthesis and Structure of Comovirus Capsids," *Prog Biophys Mol Biol.* 55:107-137 (1991).

Namba, N., et al., "Structure of Tabacco Mosaic Virus at 3.6 Å Resolution: Implications for Assembly," *Science* 231:1401-1406 (1986).

Pelham, H.R.B. and Jackson, R.J., "An Efficient mRNA-Dependent Translation System from Reticulocyte Lysates," *Eur. J. Biochem.* 67:247-256 (1976).

Rose,C. and Evans, D., "Poliovirus antigen chimeras," *TIBTECH* 9:415-421 (1991).

Rossmann et al., Icosahedral RNA Virus Structure, in *Annual Reviews of Biochemistry* 58:533-573 (1989).

Sanger, F., et al., "Cloning in Single-stranded Bacteriophage as an Aid to Rapid," *J. Mol. Biol.* 143:161-178 (1980).

Shanks, M., et al., "The Primary Structure of Red Clover Mottle Virus Middle Component RNA," *Virology* 155:697-706 (1986).

Stauffacher, C.V. et al., "The Structure of Cowpea Mosaic Virus at 3.5 Å Resolution," *Crystallography in Molecular Biol.* pp. 293-308 (1985).

Takamatsu, N., et al., "Production of enkephalin in tobacco protoplasts using tobacco mosaic virus RNA vector," *FEBS Letters* 269 (1):73-76 (1990).

van Wezenbeek, et al., "Primary structure and gene organization of the middle-component RNA of cowpea mosaic virus," *EMBO J.* 2:941-946 (1983).

Wimmer, "Genome-Linked Proteins of Viruses," *Cell* 28:199-201 (1982).

Ziegler-Graff, et al., "Biologically Active Transcripts of Beet Necrotic Yellow Vein Virus RNA-3 and RNA-4," *J. Gen. Virol.* 69:2347-2357 (1988).

\* cited by examiner

```
                                  <------ β B ------->
1           5              10            15             20              25
G  P  V  C  A  E  A  S  D  V  Y  S  P  C  M  I  A  S  T  P  P  A  P  F  S
GGACCTGTTTGTGCTGAAGCCTCAGATGTGTATAGCCCATGTATGATAGCTAGCACTCCTCCTGCTCCATTTTCA
     2670                    2700         Nhe1              2730

<------ β C ------>
                    30             35            40
D  V  T  A  V  T  F  D  L  I  N  G  K  I  T           (SEQ ID NO: 6)
GACGTTACAGCAGTAACTTTTGACTTAATCAACGGCAAAATAACT         (SEQ ID NO: 5)
                       2760
```

Figure 4

Figure 5(A)

```
  S  T  Y  S  R  N  A  V  P  N  L  R  G  D  L  Q  V  L  A  Q  K  V  A  R  T  L  P
CTAGCACTTATAGTAGAAATGCTGTTCCTAATTTGAGAGGAGATCTTCAAGTTTTGGCTCAAAAGGTTGCTCGGACTCTTC
                                              BglII
GTGAATATCATCTTTACGACAAGGATTAAACTCTCCTCTAGAAGTTCAAAACCGAGTTTCCAACGAGCCTGAGAAGGATC
                                                                    (SEQ ID NO: 9)
```

(SEQ ID NO: 7)
(SEQ ID NO: 8)

Figure 5(B)

```
  1          5              10              15              20              25
  G  P  V  C  A  E  A  S  D  V  Y  S  P  C  M  I  A  S  T  Y  S  R  N  A  V  P  N
GGACCTGTTTGTGCTGAAGCTTCTGATGTTTATAGCCCATGTATGATAGCTAGCACTTATAGTAGAAATGCTGTTCCTAAT
        2670                              2700   NheI                           (SEQ ID NO: 11)

L  R  G  D  L  Q  V  L  A  Q  K  V  A  R  T  L  P  S  T  P  P  A  P  F  S
TTGAGAGGAGATCTTCAAGTTTTGGCTCAAAAGGTTGCTCGGACTCTTCCTAGCACTCCTCCTGCTCCATTTTCA
     BglII                                              xNheI            2730
                                                                    (SEQ ID NO: 10)
```

Figure 9(A)

```
S  T  D  R  P  E  G  I  E  E  G  G  E  R  D  R  D  R  S  D      (SEQ ID NO: 17)
CTAGCACTGACCGGCCCTGAGGGCATCGAGGAAGAGAGGGGCGGTGAGCGCGATCGTGATCGTTCGGACGT   (SEQ ID NO: 16)
GTGACTGGGCGGGACTCCCGTAGCTCCTTCTCCCGCCACTCGGCTAGCACTAGCAAGCC               (SEQ ID NO: 18)
                                           Pvul
```

Figure 9(B)

```
1           5           10          15
G  P  V  C  A  E  A  S  D  V  Y  S  P  C  M  I  A  S  T  D  R  P  E  G  I  E
GGACCTGTTTGTGCTGAAGCCTCAGATGTGTATAGCCCATGTGTATGATAGCTAGCACTGACCGCCCCTGAGGGCATCGAG
                                           2700                     NheI
                                                                            <------

20          25          30          35
E  E  G  G  E  R  D  R  D  R  S  D  V  T  A  V  T  F  D  L  I              (SEQ ID NO: 20)
GAAGAGGGCGGTGAGCGCGATCGTGATCGTTCGGACGTCACAGCAGTAACTTTTGACTTAATC            (SEQ ID NO: 19)
                           PvuI     AatII                    2760
------>
```

Figure 10(A)

```
S   T   P   A   T   G   I   D   N   H   H   R   E   A   K   L   D                (SEQ ID NO: 22)
CTAGCACTCCTGCTACTGGAATCGATAATCATAGAGAAGCTAAATTGGACGT                              (SEQ ID NO: 21)
                   GTGAGGACGATGACCTTAGCTATTAGTATCTCTTCGATTTAACC                   (SEQ ID NO: 23)
                                 ClaI
```

Figure 10(B)

```
1               5                  10                 15
G   P   V   C   A   E   A   S   D   V   Y   S   P   C   M   I   A   S   T   P   A   T   G   I   D   N
GGACCTGTGTTTGTGCTGAAGCCCTCAGATGTGTATAGCCCATGTATGATAGCTAGCACTCCTGCTACTGGAATCGATAAT       ClaI
                                                              2700 NheI
2670
    <-----------------------------------
                                H   R   E   A   K   L   D   V   T   A   V   T   F   D   L   I       (SEQ ID NO: 25)
CATAGAGAAGCTAAATTGGACGTCACAGCAGTAACTTTTGACTTAATC                                                    (SEQ ID NO: 24)
          AatII
                    2760
```

MODIFIED PLANT VIRUSES AS VECTORS

In accordance with the provisions of 35 U.S.C. 120, this application claims the priority and is a continuation-in-part of U.S. patent application Ser. No. 08/137,032, filed Dec. 15, 1993 U.S. Pat. No. 6,110,466, which is a 371 of PCT/GB92/00589, filed Apr. 2, 1992, which claims benefit of the priority under 35 U.S.C. 119 of: Great Britain Patent Application No. 91 08386.5, filed Apr. 16, 1991.

This invention relates to the use of viruses as carriers (vectors) for the production or presentation of foreign peptides. More particularly, the invention relates to the genetic manipulation of viral nucleic acid by incorporation of foreign nucleic acid sequences which are expressed as peptides in the virus particle (virion). In this specification the term "foreign", as applied to a peptide or to the nucleic acid encoding therefor, signifies peptide or nucleic acid sequences which are not native to the plant virus used as a vector. Such sequences can be alternatively described as exogenous or heterologous sequences. The term "peptide" includes small peptides and polypeptides.

The use of viruses as carriers of foreign peptides has been extensively explored in the field of composite virus vaccines. Such vaccines are based on chimeric viruses which are hybrids of different animal virus components. Usually the major component of such hybrids is derived from a virus which is or has been rendered harmless and the minor component is a selected antigenic component of a pathogenic virus. For example, a pox virus such as vaccinia or an attenuated poliovirus may be used as a vector for immunogenic components of other animal viruses including human viruses.

However, the above technique has several disadvantages. Such vaccines are produced from viruses grown in cell culture systems which are expensive to design and run. The composite virus approach involves genetic manipulation of live, animal-infecting viruses, with the risk that mutations may give rise to novel forms of the virus with altered infectivity, antigenicity and/or pathogenicity. The animal virus used as the vector is often a virus to which the animal may already have been exposed, and the animal may already be producing antibodies to the vector. The vector may therefore be destroyed by the immune system before the incorporated antigenic site of the second virus induces an immune response.

The present invention avoids the above-mentioned disadvantages by the use of a radically different type of virus component in the design of chimeric viruses expressing foreign sequences. Moreover, although the invention has particular relevance to the solution of problems encountered in the production of virus vaccines, it is much wider both in concept and field of application as indicated hereinafter.

The present invention utilises plant viruses as vector systems for the expression of foreign nucleotide sequences ie nucleotide sequences (RNA or DNA) which are not present in plant viruses, as found in Nature, and which in consequence code for peptides not normally found in any naturally occurring plant virus.

The present invention comprises assembled particles of a plant virus containing a foreign peptide. The plant viruses of the present invention are therefore modified forms of the native viruses and for convenience will be referred to as modified viruses.

The foreign peptides which may be incorporated into plant viruses according to this invention may be of highly diverse types and are subject only to the limitation that the nature and size of the foreign peptide and the site at which it is placed in or on the virus particle do not interfere with the capacity of the modified virus to assemble when cultured in vitro or in vivo. In broad concept, modified viruses may be formed from any biologically useful peptides (usually polypeptides) the function of which requires a particular conformation for its activity. This may be achieved by association of the peptide with a larger molecule eg to improve its stability or mode of presentation in a particular biological system. Examples of such peptides are peptide hormones; enzymes; growth factors; antigens of protozoal, viral, bacterial, or fungal origin; antibodies including anti-idiotypic antibodies; immunoregulators and cytokines eg interferons and interleukins; receptors; adhesins; and parts or precursors of any of the foregoing types of peptide. The peptide preferably contains more than 5 amino acids.

Among the broad range of bioactive peptide sequences bound to plant virus vectors in accordance with the present invention special importance attaches to the antigenic peptides which are the basis of vaccines, particularly animal (including human) virus vaccines. For vaccine applications the invention provides an especially attractive epitope presentation system. When used for such applications the antigenic peptide component will be sited appropriately on the virus particle so as to be easily recognised by the immune system, for example by location on an exposed part of the coat protein of the virus. As applied to the latter, therefore, the present invention comprises assembled particles of a modified plant virus containing an antigen derived from a pathogen eg an animal virus, incorporated in an exposed surface of the coat protein of the plant virus. The invention also comprises the use of such assembled modified plant virus particles as the immunogenic component of a vaccine.

In U.S. Pat. No. 4,407,956 and European applications 067,553 194,809 221,044 and PCT applications WO 87/06261 and WO/90/00611 it has previously been proposed to use the DNA and RNA of certain plant viruses as vectors for the introduction of exogenous material into plants either to confer new properties on the plant itself or to enable certain valuable compounds (eg plant metabolites) to be recovered. In such prior proposals interest focuses entirely on the modified DNA or RNA of the plant virus and its use in the phenotypic transformation of plants. Most of these prior specifications are of a theoretical and speculative nature and none discloses the isolation of whole particles (virions) of a plant virus having a modified coat protein or the use of such particles for the preparation of an animal virus vaccine, or for any other purpose. In Febs Letters (1990) 269, 73–76 Takamatsu et al describe attempts to express a foreign peptide of 5 amino acids fused to the carboxy-terminus of the coat protein of tobacco mosaic virus. However, no modified plant viral particles were produced in the experiments described.

To produce modified plant virus particles in accordance with this invention the plant viral nucleic acid is modified by introducing a nucleotide sequence coding for the foreign peptide eg an animal virus antigen at that part of the plant viral genome which codes for an exposed portion of the coat protein, infecting plants or plant cells with the modified viral nucleic acid, and harvesting assembled particles of the modified virus. This procedure is best carried out by direct manipulation of the DNA of the virus in the case of DNA viruses or by manipulation of a cDNA corresponding to the RNA of an RNA virus. In the case of an RNA virus, an RNA transcript of the modified DNA is usually prepared for inoculation of plant cells or preferably whole plants so as to achieve a multiplication stage prior to the harvesting of assembled particles of the modified virus. In the case of a DNA virus, the DNA itself is introduced into the plant. In this way, the foreign peptide is initially expressed as part of the capsid protein and is thereby produced as part of the whole virus particle. The peptide may thus be produced as a conjugate molecule intended for use as such. Alternatively, the genetic modification of the virus may be designed in order to permit release of the desired peptide by the application of appropriate agents which will effect cleavage from the virus particle.

In order to produce modified virus on a commercial scale, it is not necessary to prepare infective inoculant (DNA or RNA transcript) for each batch of virus production. Instead, an initial inoculant may be used to infect plants and the resulting modified virus may be passaged in the plants to produce whole virus or viral RNA as inoculant for subsequent batches.

For the purposes of the present invention a particularly valuable group of viruses for use as vectors are those in which the nucleic acid coding for the capsid is a separate moiety from that which codes for other functional molecules and whose coat proteins have a βbarrel structure. An advantage of the use of viruses which have this structure is that the loops between the individual strands of β-sheet provide convenient sites for the insertion of foreign peptides. Modification of one or more loops is a preferred strategy for the expression of foreign peptides in accordance with the present invention. This group includes the comoviruses such as cowpea mosaic virus and bean pod mottle virus, and the nepoviruses such as tomato ringspot virus and strawberry latent ringspot virus. An advantage of the comoviruses is that their capsid contains sixty copies each of 3 different β-barrels which can be individually manipulated. Other virus groups with similar 3-dimensional structures but a single type of β-barrel include the tombusviruses and the sobemoviruses. Other groups of plant and animal viruses which share structural similarities but whose coat proteins do not have a β-barrel structure may also be modified in accordance with this invention, for example the plant and animal rhabdoviruses.

The foreign RNA or DNA may be inserted into the plant virus genome in a variety of configurations. For example, it may be inserted as an addition to the existing nucleic acid or as a substitution for part of the existing sequence, the choice being determined largely by the structure of the capsid protein and the ease with which additions or replacements can be made without interference with the capacity of the genetically-modified virus to assemble in plants. Determination of the permissible and most appropriate size of addition or deletion for the purposes of this invention may be achieved in each particular case by experiment in the light of the present disclosure. The use of addition inserts appears to offer more flexibility than replacement inserts in some instances.

In accordance with this invention, multiplication of modified virus and production of significant yields thereof in plant hosts is an important part of the novel strategy of the invention to produce antigens for vaccines and other types of peptide in an advantageous manner. As indicated above, the inserted heterologous nucleotide sequence may include those coding for amino acids which are readily cleaved so that, after the multiplication stage, the desired material may be separated from the virus particles. As an alternative to total cleavage of the peptide, it may be possible and desirable in some cases to release the peptide in a form in which it remains intact within a major part of the capsid but separated from the viral nucleic acid.

Included among the many epitopes which can be expressed on the surface of the CPMV capsids are those from picornaviruses such as foot-and-mouth disease virus (FMDV), poliovirus, human rhinovirus (HRV) and hepatitis A virus (HAV), epitopes associated with either gp41 or gp120 of human immunodeficiency virus (HIV) and the epitope derived from the major coat protein of human papillomavirus (HPV).

As applied to the preparation of vaccines, the present invention has many advantages over conventional vaccines, recombinant vaccines based on animal viruses, and peptide vaccines, for example:

1. Lower production costs, as very high yields of pure virus are obtainable from infected plants, and no tissue culture production step is necessary.
2. Improved safety, as plant viruses are incapable of infecting and replicating in animals, and thus will not be able to mutate into virulent forms, as may be the case with conventional and recombinant animal virus vaccines.
3. Some plant viruses, particularly comoviruses, are exceptionally stable, and purified preparations can be dried and stored for many years at room temperature without losing infectivity. This property will allow the development of slow-release vaccines, reducing the number of injections required to maintain immunity.
4. Animals are unlikely to have been exposed to plant viruses, and therefore will not already have antibodies to the vector, thus increasing the effectiveness of the composite vaccine.
5. The plant viruses, being smaller than most of the animal viruses which have been previously used as vectors eg vaccinia, allow the introduction of chimeric genes by in vitro manipulation as contrasted with homologous recombination in vivo (transfection).

To demonstrate this system, the plant virus cowpea mosaic comovirus (CPMV) was chosen. The three-dimensional structure of the CPMV has been solved at atomic resolution which has enabled identification of sites suitable for modification without disruption of the particle structure.

To demonstrate the wide applicability of this invention, antigenic sites of three different animal viruses were used. Two were viruses belonging to the picornavirus group of animal viruses—foot and mouth disease virus (FMDV) and human rhinovirus (HRV). There are several important pathogens in this group, particularly FMDV, poliomyelitis (polio) and hepatitis A.

The third virus selected was human immune deficiency virus (HIV) which bears no similarity to any known plant virus, and for which no successful vaccines are currently available.

Figure 1B:
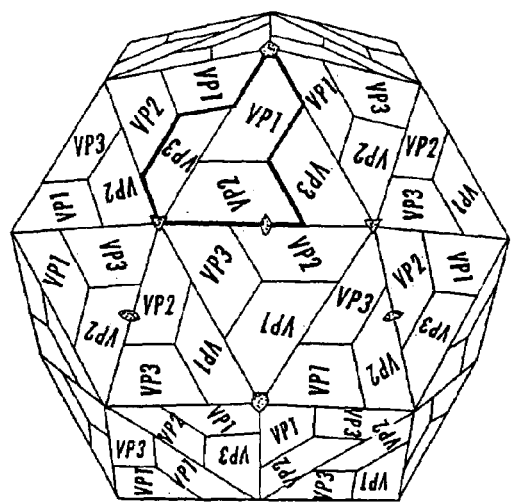
Figure 1C:
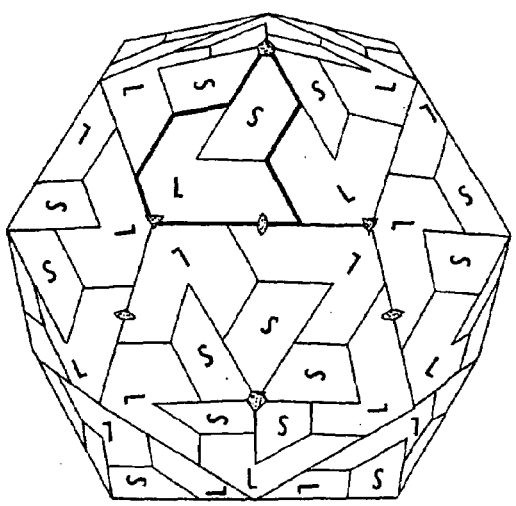

The invention will now be further described with reference to the following accompanying drawings:

FIG. 1 depicts a comparison of the structures of simple T=3 virus, picornavirus and comovirus capsids. In each case, one trapezoid represents one β-barrel. Thus the large (L or VP37) capsid protein of comoviruses consists of two covalently linked β-barrels which are equivalent to the C and B-type subunits of a T=3 virus or VP2 and VP3 of picornaviruses. The small (S or VP23) capsid protein of comoviruses contains a single β-barrel which corresponds to the A-type subunits of a T=3 virus or VP1 of a picornavirus.

Figure 2:
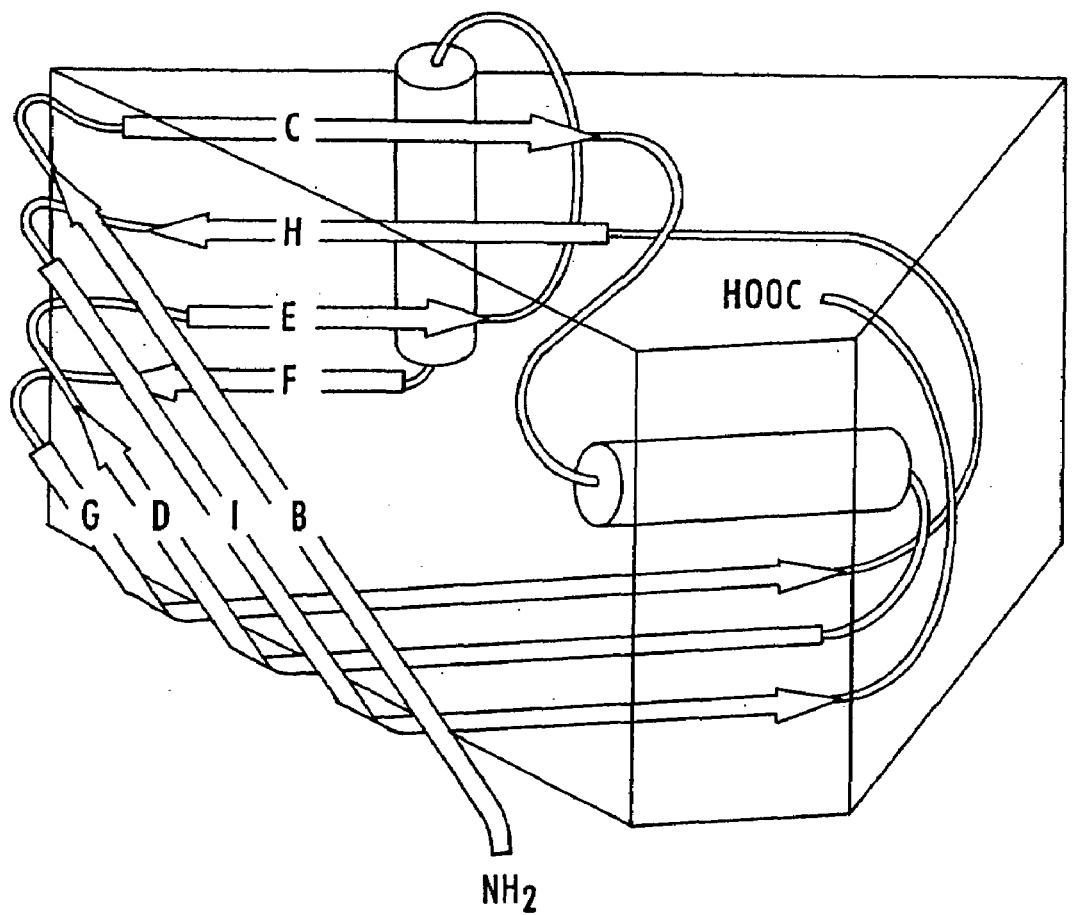

FIG. 2 depicts the secondary structure and connectivity of a canonical β-barrel. The individual strands of βsheet are labelled B through G and the amino—($NH_2$) and carboxy—(COOH) termini of the protein are indicated.

Figure 3A:
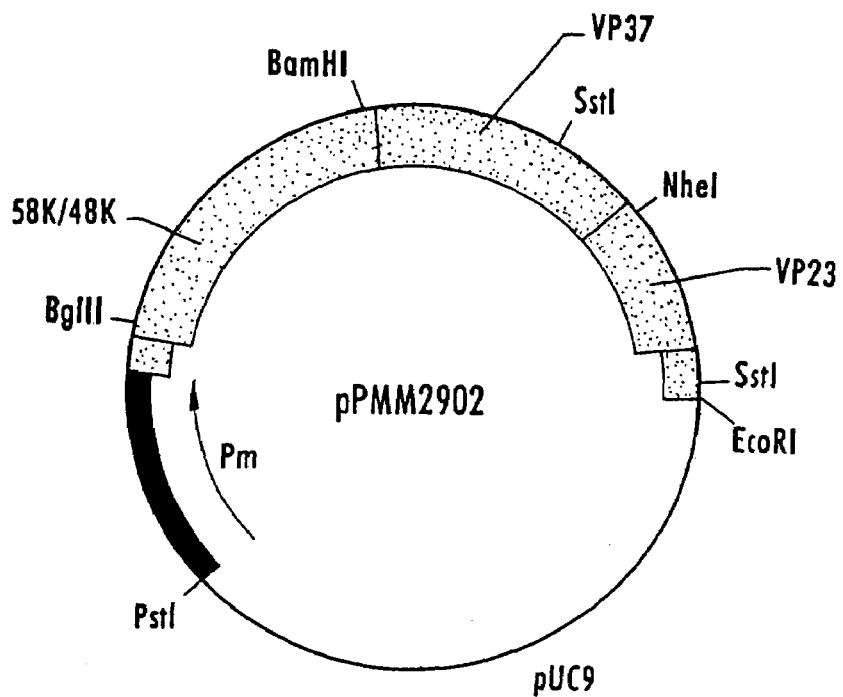
Figure 3B:
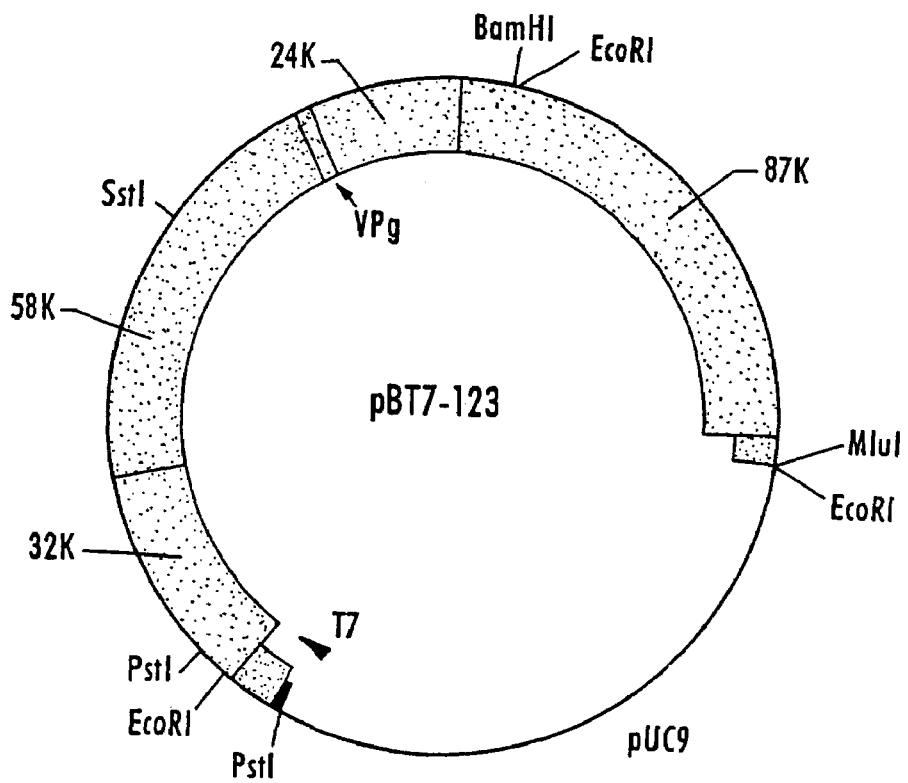

FIGS. 3a and 3b depicts (A) pPMM2902 and (B) pBT7-123. The stippled regions represent the CPMV-specific regions of the plasmids with the coding regions being indicated by the wider portions on which the various virus-encoded proteins are marked. Relevant restriction enzyme sites are indicated. Details of the construction of the plasmids are given in Holness, et al., (1989) and Dessens and Lomonossoff (1991).

FIG. 4 (SEQ ID NOS: 1 and 2) depicts the region of CPMV M RNA which encodes the amino-terminal 40 amino acids of VR23. The numbers below the nucleotide sequence refer to the M RNA sequence and the position of the unique Nhe1 site is indicated. The amino acids involved in forming the βB and βC strands of VP23 are indicated above the amino acid sequence of the protein which is shown using the standard one-letter code.

FIGS. 5a and 5b depicts (A) the nucleotide sequence (SEQ ID NO: 3) of the oligonucleotides used in the construction of pFMDV together with the amino acid sequence (SEQ ID NO: 4) encoded by the top (positive) strand and (B) the structure of VP23 after insertion of the FMDV-specific oligonucleotides SEQ ID NOS: 5 and 6). The arrowed region indicates the extent of the inserted FMDV epitope. The Nhe1 site not restored during the cloning is indicated by xNhe1. The diagnostic Bgl11 site present in the inserted sequence is also indicated.

FIG. 8 (SEQ ID NOS:7 to 10) depicts the construction of a "substitution" vector by site-directed mutagenesis. The asterisk indicates the T residue that is changed to a C by site-directed mutagenesis, thereby creating a novel Aat11 site.

FIGS. 9*a* and 9*b* depicts (A) the nucleotide sequence (SEQ ID NO: 11) of the oligonucleotides used in the construction of pMT7-HIV together with the amino acid sequence (SEQ ID NO:12) encoded by the top (positive) strand and (B) the structure of VP23 after insertion of the HIV-specific oligonucleotides (SEQ ID NOS:13 and 14). The arrowed region indicates the extent of the inserted HIV epitope. The diagnostic Pvu1 site present in the inserted sequence is also indicated.

FIGS. 10*a* and 10*b* depicts (A) the nucleotide sequence (SEQ ID NO: 15) of the oligonucleotides used in the construction of pMT7-HRV together with the amino acid sequence (SEQ ID NO: 16) encoded by the top (positive) strand and (B) the structure of VP23 after insertion of the HRV-specific oligonucleotides (SEQ ID NOS:17 and 18). The arrowed region indicates the extent of the inserted HRV epitope. The diagnostic Cla1 site present in the inserted sequence is also indicated.

FIG. 11 depicts the construction of plasmids pMT7-HIV and pMT7-HRV. The representation of the various CPMV-specific regions is as in FIG. 3. The HIV- and HRV-specific regions inserted into VP23 are shown as the black segment in the CPMV-specific coding, region.

FIG. 12 depicts a "Western blot" of protein extracts of the leaves of five cowpea plants (lanes A to E) inoculated with a mixture of pMT7-FMDV-1 and PBT7-123 transcripts. The blot was probed with serum specific for the FMDV epitope. Lanes "mock" and "wt" contain extracts of leaves which were either mock-inoculated or inoculated with wild-type CPMV RNA, respectively. The lane marked "virus" contains purified wild-type CPMV. The sizes of marker proteins are shown on the right-hand side of the blot.

Comoviruses

Comoviruses are a group of at least fourteen plant viruses which predominantly infect legumes. Their genomes consist of two molecules of single-stranded, positive-sense RNA of different sizes which are separately encapsidated in isometric particles of approximately 28 nm diameter. The two types of nucleoprotein particles are termed middle (M) and bottom (B) component as a consequence of their behaviour in caesium chloride density gradients, the RNAs within the particles being known as M and B RNA, respectively. Both types of particle have an identical protein composition, consisting of 60 copies each of a large (VP37) and a small (VP23) coat protein. In addition to the nucleoprotein particles, comovirus preparations contain a variable amount of empty (protein-only) capsids which are known as top (T) component.

In the case of the type member of the comovirus group, cowpea mosaic virus (CPMV), it is known that both M and B RNA are polyadenylated and have a small protein (VPg) covalently linked to their 5' terminus. More limited studies on other comoviruses suggest that these features are shared by the RNAs of all members of the group. Both RNAs from CPMV have been sequenced and shown to consist of 3481 (M) and 5889 (B) nucleotides, excluding the poly (A) tails (van Wezenbeek et al. 1983; Lomonossoff and Shanks, 1983). Both RNAs contain a single, long open reading frame, expression of the viral gene products occurring through the synthesis and subsequent cleavage of large precursor polypeptides. Though both RNAs are required for infection of whole plants, the larger B RNA is capable of independent replication in protoplasts, though no virus particles are produced in this case (Goldbach et al., 1980). This observation, coupled with earlier genetic studies, established that the coat proteins are encoded by M RNA.

A 3.5 Å electron density map of CPMV shows that there is a clear relationship between CPMV and the T=3 plant viruses such as the tombusviruses, in particular tomato bushy stunt (TBSV) and the sobemoviruses, in particular southern bean mosaic (SBMV). The capsids of these latter viruses are composed of 180 identical coat protein subunits, each consisting of a single β-barrel domain. These can occupy three different positions, A, B and C, within the virions (FIG. 1). The two coat proteins of CPMV were shown to consist of three distinct β-barrel domains, two being derived from VP37 and one from VP23. Thus, in common with the T=3 viruses, each CPMV particle is made up of 180 β-barrel structures. The single domain from VP23 occupies a position analogous to that of the A type subunits of TBSV and SBMV, whereas, the N- and C-terminal domains of VP37 occupy the positions of the C and B type subunits respectively (FIG. 1).

X-ray diffraction analysis of crystals of CPMV and another member of the group, bean pod mottle virus (BPMV) shows that the 3-D structures of BPMV and CPMV are very similar and are typical of the comovirus group in general.

In the structures of CPMV and BPMV, each β-barrel consists principally of 8 strands of antiparallel β-sheet connected by loops of varying length. The connectivity and nomenclature of the strands is given in FIG. 2. The flat β-sheets are named the B,C,D,E,F,G,H and I sheets, and the connecting loops are referred to as the βB-βC, βD-βE, βF-βG and βH-βI loops. The comoviruses are also structurally related to the animal picornaviruses. The capsids of picornaviruses consist of 60 copies of each of three different coat proteins VP1, VP2 and VP3 each one consisting of a single β-barrel domain. As in the case of comoviruses, these coat proteins are released by cleavage of a precursor polyprotein and are synthesised in the order VP2-VP3-VP1. Comparison of the 3-dimensional structure of CPMV with that of picornaviruses has shown that the N- and C-terminal domains of VP37 are equivalent to VP2 and VP3 respectively and that VP23 are equivalent to VP1 (FIG. 1). The equivalence between structural position and gene order suggests that VP37 corresponds to an uncleaved form of the two picornavirus capsid proteins, VP2 and VP3.

One of the principal differences between the comoviruses and picornaviruses is that the protein subunits of comoviruses lack the large insertions between the strands of the β-barrels found in picornaviruses though the fundamental architecture of the particles is very similar. The four loops (βB-βC, βD-βE, βF-βG and βH-βI see FIG. 2) between the β-sheets are not critical for maintaining the structural integrity of the virions but, in accordance with this invention, are used as sites of expression of foreign peptide sequences, such as antigenic sites from animal viruses.

Modification of CPMV Virus

In order to make insertions into the coat protein of CPMV, it is necessary to have a means of manipulating the genome of the virus. A full-length cDNA clone of CPMV M RNA (pPMM2902) in the transcription vector pPMI was available (see FIG. 3A) (Ahlquist and Janda, 1984, Holness et al. (1989) and Holness (1989). We have shown that transcripts from pPMM2902 can multiply when electroporated in cowpea mesophyll protoplasts in the presence of highly purified virion B RNA, therefore allowing modifications to be made to the viral coat proteins without affecting the multiplication and assembly of the virus.

In view of the possible danger that B RNA purified from virions to provide the proteins required for viral replication with pPMM2902 might be cross-contaminated with wild-type M RNA, we have constructed a full-length cDNA clone of B RNA, pBT7-123 (see FIG. 3B). The full-length copy of B RNA is immediately downstream of a modified T7 promoter. Following linearisation with the restriction enzyme MIu1, transcripts identical in size to natural B RNA can be synthesised by T7 RNA polymerase. A mixture of transcripts from pPMM2902 and pBT7-123 gives rise to a full virus infection when electroporated into cowpea protoplasts, and therefore replaces the use of natural B RNA.

We have selected the βB-βC loop in VP23 for the insertion of foreign peptide. This loop is clearly exposed on the surface of the viral particle and computer modelling has shown that even large loops inserted at this site are unlikely to interfere with the interaction between adjacent subunits responsible for capsid structure and stability. This loop has a unique Nhe1 site at position 2708 of the M RNA-specific sequence where foreign sequences may be inserted (see FIG. 4).

The principle antigenic sites of the picornavirus foot and mouth disease (FMDV) and human rhinovirus (HRV), and the lentiretrovirus human immune deficiency virus (HIV) were used to illustrate the use of this invention in the production of vaccines to animal viruses.

Figure 6:
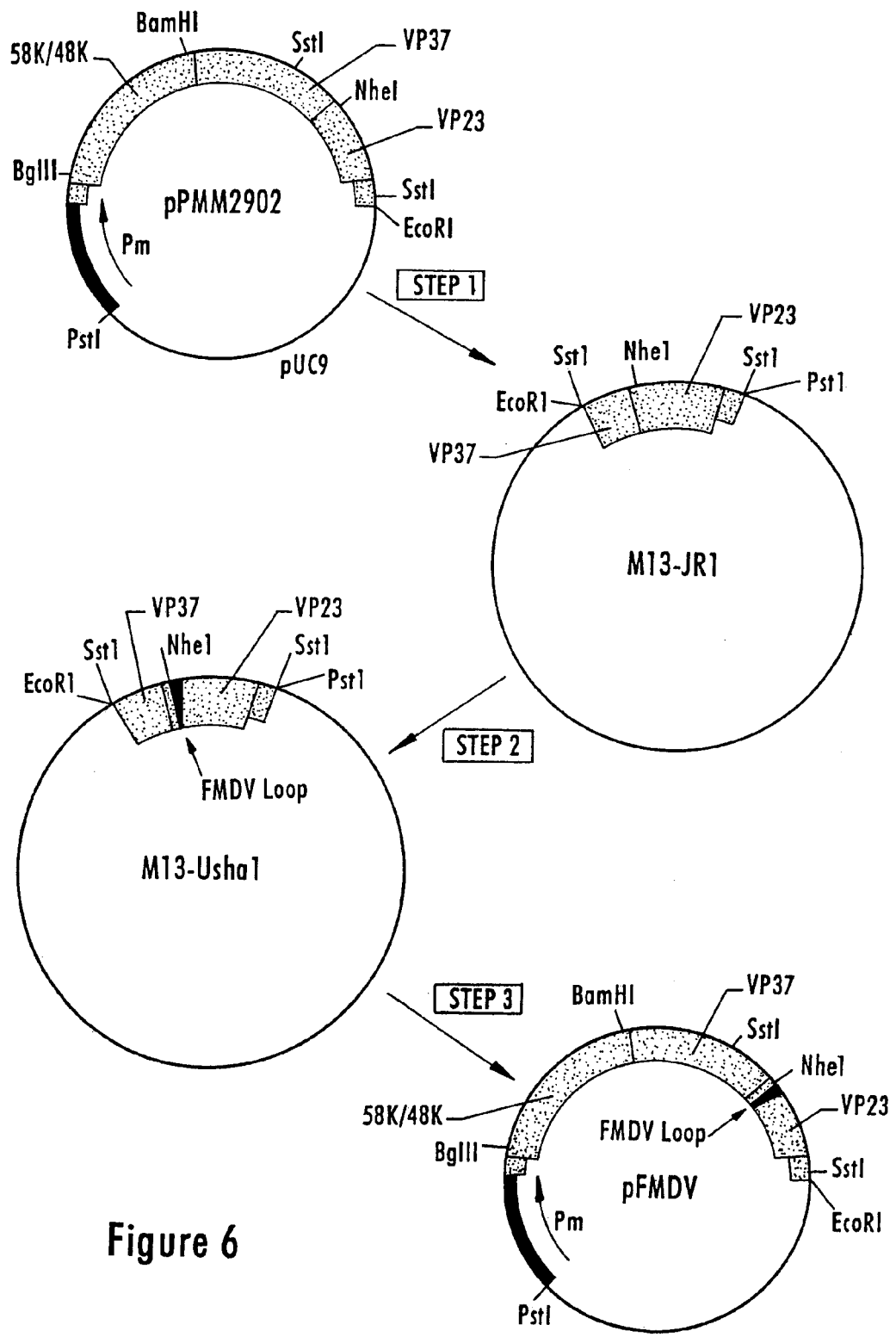

Design and Construction of pFMDV, a Full Length cDNA Clone of CPMV M RNA Containing a DNA Insert Coding for a Segment of FMDV Loop Protein To insert the "FMDV loop" into the βB-βC loop of VP23 of CPMV, two complementary oligonucleotides, both 81 residues long, were chemically synthesised. Their sequences are given in FIG. 5A. The positive sense oligonucleotide contains the sequence encoding amino acid residues 136–160 from VP1 of FMDV serotype $O_1$ strain BFS 1860. The nucleotide sequence of oligonucleotides was designed to take account of the codon usage preference found in CPMV and includes a Bgl11 site in the middle of the sequence to facilitate screening. When annealed, the oligonucleotides give a double-stranded DNA sequence with Nhe1-compatible ends. Thus the oligonucleotides can be inserted into the unique Nhe1 site of pPMM2902. The effect of such an insertion on the sequence of the VP23 is shown in FIG. 5B. To facilitate the insertion of the FMDV loop, the FMDV-specific oligonucleotides were initially ligated into an M13 sub-clone of pPMM2902 which contained the sequence encoding VP23. This was done to enable clones harbouring the FMDV-specific sequence to readily be identified by sequence analysis. All the standard DNA manipulations were carried out according to Maniatis et al (1982). Details of the construction of pFMDV are given below and are shown diagrammatically in FIG. 6.

STEP 1. The plasmid pPMM2902 was digested with the restriction enzyme Sst1 which cuts twice within the CPMV M RNA-specific sequence at positions 2296 and 3423 but does not cut within the sequence of the plasmid pPM1. Following agarose gel electrophoresis, and both the large (6.0 kb) the small (1.1 kb) fragment were purified by electroelution from the gel. The 1.1 kb Sst1 fragment was ligated into the Sst1-cut, phosphatase-treated replicative form DNA from the bacteriophage M13mp18. The ligation mixture was used to transform *E. coli* strain JM101 using the calcium chloride procedure. Plaques containing the 1.1 kb Sst1 fragment from M RNA were identified by the Lac complementation assay and DNA sequence analysis and one, M13-JR1 was selected for further work.

STEP 2. The double-stranded replicative form DNA of M13-JR1 was isolated from infected *E. coli* strain JM101 cells by the method of Birnboim and Doly (1979). The purified DNA was linearised by digestion with the restriction enzyme Nhe1 and the linearised plasmid treated with calf intestinal phosphatase. The two oligonucleotides with Nhe1-compatible termini encoding amino acid residues 136 to 160 of VP1 from FMDV were phosphorylated with ATP using polynucleotide kinase and annealed to each other by boiling and slow cooling. The annealed oligonucleotides were ligated into Nhe-1-digested M13-JR1, the ligation mixture used to transform *E. coli* strain JM101 and the transformation mixture plated out on a lawn of JM101. A large number of plaques were found on the plates, 20 of which were selected for sequence analysis. Bacteriophage were propagated in JM101 and the single-stranded DNA isolated exactly as described by Sanger et al (1980). The nucleotide sequence of the region of the bacteriophage DNA around the Nhe1 site was determined by the dideoxy method as modified by Biggin et al (1983), using an 18mer, 5'AGT-TAC-TGC-TGT-AAC-GTC-3' (SEQ ID NO:19), complementary to nucleotides. 2735–2752 of the M RNA sequence, as primer. Of the plaques analysed, one, designated M13-usha1, had a single copy of the desired sequence in the correct orientation.

STEP 3. M13-usha1 was propagated in *E. coli* strain JM101 and the replicative form DNA was isolated from the infected cells by the method of Birnboim and Doly (1979). The DNA was digested with Sst1 and the 1.1 kb fragment purified by agarose gel electrophoresis. This fragment was ligated to the large (6.0 kb) Sst1 fragment from pPMM2902 (see above) which had been treated with calf intestinal phosphatase. The ligation mixture was used to transform *E. coli* strain JM83 using the calcium chloride method. The transformation mixture was plated out on L-agar plates containing 100 µg/ml carbenicillin and the plates incubated overnight at 37° C. 12 carbenicillin-resistant colonies were selected for further study. The colonies were grown up as 1 ml cultures in L-broth, plasmid "minipreps" prepared and analysed by restriction enzyme digestion. From the patterns obtained by digestion with the enzymes Sst1, Bgl11 and EcoRV, it was possible to deduce that 4 colonies consisted of full-length clones of CPMV containing the sequence of the FMDV-specific oligonucleotides in the correct orientation. One of these, pFMDV, was subsequently propagated on a large scale and the plasmid DNA was isolated by the method of Birnboim and Doly (1979) and further purified by centrifugation using caesium chloride/ethidium bromide gradients (Maniatis et al (1982).

Properties of PFMDV Transcripts

1. Purified pFMDV DNA was linearised by digestion with EcoR1 and transcribed using *E.coli* RNA polymerase exactly as described for pPMM2902 by Holness et al (1989). Electrophoresis of the products of formaldehyde-containing agarose gels (Lehrach et al., 1977) revealed the presence of transcripts which co-migrated with authentic viral M RNA.

2. Following treatment with DNAse1 and lithium chloride precipitation to remove the template DNA, the transcripts were translated in vitro in the message-dependent rabbit reticulocyte system (Pelham and Jackson 1976) in the presence of $^{35}$S-methionine. The products were examined by electrophoresis on polyacrylamide gels containing SDS (Laemmli, 1970) and visualised by autoradiography of the dried-down gel. The autoradiographs revealed the presence of two proteins of 105 and 95 kDa which co-migrated with the translation products of natural M RNA.

3. The ability of transcripts of pFMDV to be replicated in plant cells was examined as follows: Cowpea mesophyll protoplasts were prepared as described by de Varennes et al (1985). Transcripts from pFMDV were mixed with transcripts from pBT7-123 (the plasmid containing a full-length copy B RNA) and electroporated into the protoplasts as described by Holness et al (1989). As control, a sample of the same preparation of protoplasts were electroporated with a mixture of transcripts from pBT7-123 and pPMM2902. 72 hours post-electroporation the protoplasts were harvested and the nucleic acids were extracted as described by de Varennes et al (1985). Samples of the RNA were electrophoresed on formaldehyde-containing agarose gels (Lehrach et al, 1977) and the nucleic acids blotted on to Hybond N membranes (Amersham International). The nucleic acids were cross-linked to the membranes by irradiation with u.v. light. The membranes were probed for M RNA sequences using a Hind111 fragment form pPMM2902 corresponding to nucleotides 482–2211 of the M RNA which had been labelled with $^{32}$P as described by Feinberg and Vogelstein (1983). Samples from protoplasts electroporated with pBT7-123 and either pPMM2902 or pFMDV-1 revealed the presence of M RNA-specific sequences confirming that the presence of the sequence encoding the FMDV loop did not prevent the transcripts from replicating. To confirm that the progeny of pFMDV replication retained the sequence encoding the FMDV loop, replicate membranes were probed with the positive-sense FMDV oligonucleotide which had been "oligo-labelled" (Feinberg and Vogelstein, 1983) to give a (+) sense-specific probe. The sample from protoplasts electroporated with a mixture of pBT7-123 and pFMDV transcripts gave a clear signal at the expected position for M RNA, a signal which was absent from the pPMM2902 control.

4. To establish that protein subunits containing the FMDV loop assemble into virions, extracts from infected protoplasts were examined for the presence of virus particles by immunosorbent electron microscopy. Samples of protoplasts electroporated with a mixture of transcripts from pBT7-123 and pFMDV were lysed by repeated passage through a 23 gauge needle. The extracts were centrifuged in an Eppendorf microfuge and supernatant retained for examination. 10 microlitre samples of the supernatants were incubated with gold electron microscope (em) grids which had been coated with anti-CPMV antiserum. After washing and staining with uranyl acetate, the grids were examined using a JEOL 1200 electron microscope. Particles of diameter 28 nm could be seen which had the characteristic appearance of CPMV virions. This demonstrates that the presence of the FMDV loop in VP23 does not prevent virus assembly.

Figure 7:
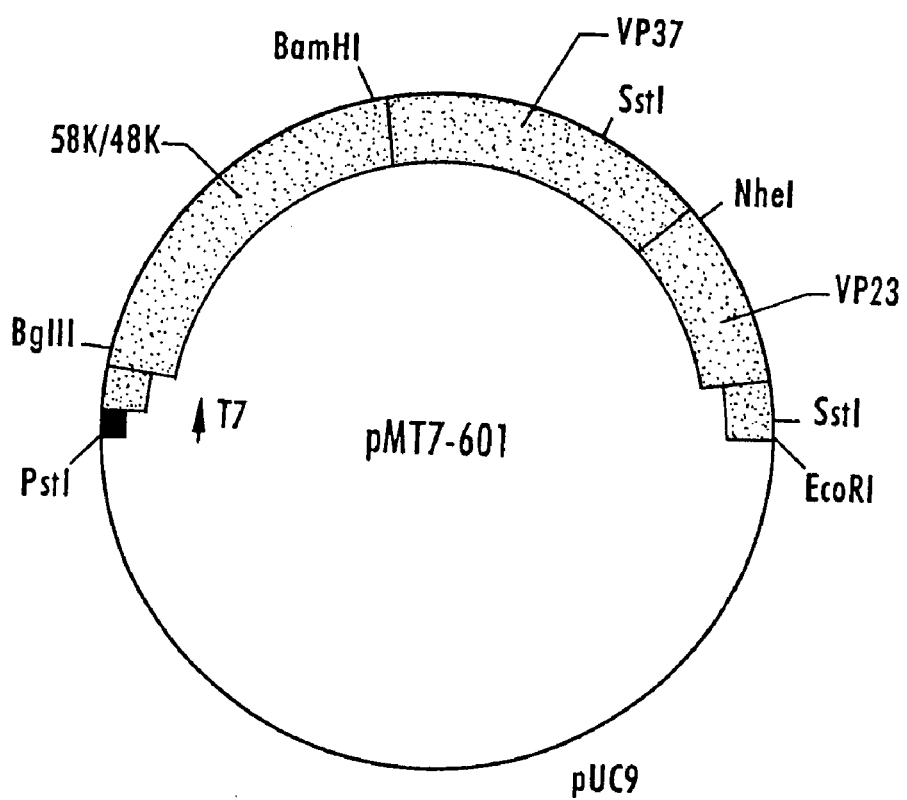

The foregoing description establishes that plant viruses modified in accordance with this invention can multiply and assemble into virus particles when electroporated into plant protoplasts. To produce modified plant viruses on a large scale it is necessary to prepare a construct which can be inoculated directly onto whole plants, and which will replicate and assemble into virus particles as in the above described protoplast system. We have therefore modified pPMM2902 in such a way that the resulting transcripts incorporate a "cap" structure at their 5' ends, and RNA synthesis is driven by a more efficient promoter. The steps in the modification of pPMM2902 to produce pMT7-601 (FIG. 7) are described in detail below.

Development of a System Capable of Infecting Whole Cowpea Plants

Construction of pMT7-601

1. 1 st strand cDNA to purified CPMV M RNA was synthesised exactly as described by Lomonossoff et al (1982), using pdT$_{12-18}$ as a primer. 2nd strand synthesis was primed using the following oligonucleotide:

```
                                          (SEQ ID NO:20)
     Pst1        T7 Promoter  ↓ 5' end M RNA
5' CCCTGCAGTAATACGACTCACTATAGTATTAAAATCTTAATAG
```

Conditions for synthesis were as described in Lomonossoff et al (1982) and Shanks et al (1986).

2. The double-stranded cDNA was digested with the restriction enzymes Pst1 and BamH1(which cleaves the M RNA sequence at position 1504) and the 1.5 kb Pst1/BamH1 fragment ligated into Pst1/BamH1 digested M13 mp18. The ligation mix was used to transform *E. coli* strain JM101. Recombinant phage harbouring inserts were identified by the ac complementation assay and checked for the presence of the correct insert by "T-track" analysis (Sanger et al., 1980) as modified by Biggin et al (1983). One clone, M13-MT7-6, was selected for further analysis and the sequence of the 5' terminal 200 nucleotides of M RNA specific sequence was determined as described by Biggin et al (1983) and shown to be identical to the equivalent sequence in pPMM2902.

3. The double-stranded, replicative DNA was isolated from *E. coli* JM101 cells infected with M13-MT7-6 by the method of Birnboim and Doly (1979). The double stranded DNA was digested with Pst1 and Bgl1 (which cuts the M RNA sequence at position 189) and the 200 bp fragment released was purified by electrophoresis on and electroelution from an agarose gel (Maniatis et al (1982).

4. The plasmid pPMM2902 (Holness et al 1989) was digested with Pst1 and Bgl11 to produce two DNA fragments of 1.1 and 6.0 kb. The smaller (1.1 kb) fragment contains the sequence of the *E. coli* promoter linked to the first 189 nucleotides of the sequence of CPMV M RNA while the larger (6.0 kb) fragment the rest of the sequence of M RNA linked to pUC9. The digest was treated with calf intestinal phosphatase, the two fragments separated by agarose gel electrophoresis and the 6.0 kb fragment recovered by electro-elution.

5. The 200 bp Pst1/Bgl11 from M13-MT7-6 and the 6.0 kb fragment from pPMM2902 were ligated together (Maniatis et al, 1982) and the mixture used to transform E. coli strain JM83. A number of carbenicillin-resistant colonies were identified and one, pMT7-601, was shown to have the desired structure. Large-scale quantities of plasmid pMT7-601 were therefore prepared as described for pFMDV.

6. After linearisation with EcoR1, plasmid pMT7-601 could be transcribed using T7 RNA polymerase to give RNA which was identical in size to natural virion M RNA when analysed on formaldehyde-containing agarose gels (Lehrach et al. 1977). The yield of transcript was approximately 1 µg of full-length M transcript per µg of linearised template DNA.

7. When a mixture of T7 transcripts from pMT7-601 and pBT7-123 was electroporated into cowpea mesophyll protoplasts, Northern blot analysis of progeny RNA revealed that transcripts from pMT7-601 are biologically active. The methods used for protoplast isolation and nucleic acid analysis were identical to those used to analyse the biological properties of pFMDV.

Infectivity of a Mixture of Capped pBT7-123 and pMT7-601 Transcripts on Cowpea Plants Samples of pBT7-123 and pMT7-601 were linearised with Mlu1 and EcoR1 respectively. Portions of the linearised templates were transcribed using T7 RNA polymerase in the presence of GpppG essentially as described by Ziegler-Graaf et al (1988). The transcription reactions contained 0.1 mg/ml linearised DNA template, 40 mM Tris-HCl pH 8.0, 25 mM NaCl, 8 mM MgCl$_2$, 2 mM spermidine hydrochloride, 0.5 mM each of UTP, ATP and CTP, 0.025 mM GTP, 0.5 mM GpppG, 0.05 mg/ml BSA, 10 mM DTT, 200 units/ml RNAguard and transcription was initiated by the addition of T7 RNA polymerase to a final concentration of 1400 units/ml. Incubation was at 37C for 2 hours. At 30, 60 and 90 minutes portions (5 µl per 1 ml transcription reaction) of a 5 mM solution of GTP were added. Following transcription, EDTA was added to 15 mM final concentration and the integrity of the transcripts was checked by electrophoresis on formaldehyde-containing agarose gels. The transcription mixtures were extracted with 2 volumes of phenol/chloroform (1.1 v/v) and the nucleic acids precipitated twice with ethanol. The nucleic acids were harvested by centrifugation, washed with ethanol and dried under vacuum. The nucleic acids were dissolved in 50 mM Tris-phosphate, pH 8.0 for inoculation on to plants.

The primary leaves of 10 day-old cowpea (Vigna unguiculata var. California blackeye) were dusted with carborundum and a 1:1 (w/w) mixture of transcripts derived from pMT7-601 and pBT7-123 were applied to the leaves with gently rubbing. A variety of transcript concentrations were used but in all cases the final inoculum volume was 50W. The results obtained showed that when a total of 5 µg of each transcript was applied per primary leaf, 100% of plants inoculated routinely developed symptoms characteristic of a CPMV infection. The presence of CPMV-specific sequences in both the inoculated and upper leaves of such plants was confirmed by "Dot blot" analysis. Samples of the inoculated and trifoliate leaves were taken using a number 10 cork borer and macerated and extracted with 0.4 mls of 10 mM sodium phosphate. The samples were centrifuged and 5 µl of the supernatant was applied to nitrocellulose filters pre-wetted wetted with 20×SSC. The nucleic acid were cross-linked to the membranes by irradiation with u.v. light and probed for M RNA-specific sequences using a $^{32}$p "oligo-labelled" (Feinberg and Vogelstein, 1983) probe consisting of nucleotides 482-2211 of the M RNA sequence. The conditions for hybridisation and washing of the filters were as described by Maniatis et al (1982). After drying, the filters were autoradiographed. A strong hybridisation signal indicated the presence of CPMV-specific sequences.

Construction of pMT7-FMDV-I, pMT7-HIV and pMT7-HRV

To construct pMT7-FMDV-I, pMT7-601 and pFMDV were both digested with restriction enzyme Sst1, the digest from pMT7-601 being subsequently treated with calf intestinal phosphatase. Sst1 cuts each plasmid twice at positions 2296 and 3423 of the M RNA-specific region to release a 1.1 kb fragment. As discussed previously this Sst1 fragment contains the region of VP23 encompassing the βB-βC loop where the FMDV loop insertion has been made. Following electrophoresis on an agarose gel, the 1.1 kb fragment from pFMDV and the 5.1 kb fragment, encompassing the vector sequence and all the rest of the M RNA specific sequence, from pMT7-601 were recovered by electo-elution. The two Sst1 fragments were ligated together and the mixture transformed in E. coli strain JM83. A number of carbenicillin-resistant colonies were picked, "minipreps" made and the plasmid DNA examined by restriction enzyme digests to identify recombinants containing the FMDV loop. One such clone was identified, designated pMT7-FMDV-1 and grown up on a large scale. All the DNA manipulations were as described for the construction of pFMDV and pMT7-601.

Figure 8:
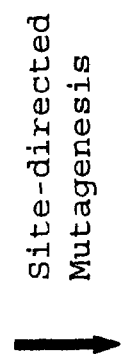

Both pFMDV and its derivative pMT7-FMDV-I have a straightforward insertion into the βB-βC loop of VP23. To limit the increase in size of the loop upon insertion of a foreign sequence, a replacement vector was designed where the foreign sequence would replace the natural βB-βC loop in VP23 rather than be added to it. In the nucleotide sequence of the region of the CPMV genome encoding VP23 a single silent base change (U to C) at position 2740 creates a unique Aat11 site at amino acid valine 27. The change in the sequence of M RNA is shown in FIG. 8. The creation of the Aat11 site enables the nucleotide sequence encoding the six amino acids from the native βB-βC loop in CPMV to be removed by digestion with Nhe1 and Aat11. The sequence can then be replaced by any sequence with Nhe1- and Aat11-compatible ends.

Two different sequences were designed to be substituted for the sequence between the Nhe1 and Aat11 sites of the mutated M RNA sequence. The first sequence to be substituted into VP23 consisted of oligonucleotides encoding residues 735–752 from the transmembrane glycoprotein gp41 from human immunodeficiency virus (HIV-1). This sequence was selected as a synthetic peptide for this region is recognised in enzyme-linked immunosorbent assays (ELISA) by antisera from seropositive AIDS patients and is capable of inducing antibodies which neutralise a range of HIV-1 isolates (Kennedy et al, 1986; Chanh et al, 1986; Dagleish et al, 1988). The second sequence consists of the nucleotide sequence encoding residues 85–99 from VP1 of human rhinovirus 14 (HRV14). In both cases, the oligonucleotides were designed to contain restriction enzyme sites to facilitate screening. The sequences of the oligonucleotides and the effect of the substitutions on the amino acid sequence of VP23 are shown in FIGS. 9 and 10. The steps in the construction of pMT7-HIV and pMT7HRV are given below and are shown diagrammatically in FIG. 11.

STEP 1. M13-JR-1 (see FIG. 6) was propagated in *E. coli* strain CJ236 and dU-containing single-stranded DNA isolated as described by Kunkel (1985). The T to C mutation at position 2740 of the M RNA sequence was made by oligonucleotide-directed mutagenesis of dU-containing single-stranded M13-JR1 DNA using the primer CTG-CTG-TGA-CGT-CTG-AAA-A (SEQ ID NO:21) as described by Kunkel (1985). This resulted in the construction of clone M13-JRAat11. The mutation was confirmed by dideoxy sequence analysis of single-stranded DNA (Biggin et al, 1983) and by restriction enzyme digestion of the double-stranded replication form DNA.

STEP 2. The replicative form DNA of M13-JRAat11 was isolated and digested with Nhe1 and Aat11 and treated with calf intestinal phosphatase. The pairs of oligonucleotides shown in FIGS. 9 and 10 were phosphorylated with ATP using polynucleotide kinase, annealed together by boiling and slow cooling and ligated into Nhe1/Aat11-digested M13-JRAat11. Recombinant M13 clones harbouring the inserted sequences were identified by sequence analysis of the single-stranded bacteriophage DNA exactly as described previously for pFMDV. Two clones, M13-HIV and M13-HRV containing the required sequences were identified and the double-stranded replicative form DNA was isolated shown to give the expected pattern of fragments on restriction enzyme digestion.

STEP 3. Replicative form DNA from M13-HIV and M13-HRV was digested with Sst1 and the 1.2 kb M RNA-specific fragment recovered by electro-elution after electrophoresis of the digest on an agarose gel. The 1.2 kb fragments were ligated into the large Sst1 fragment from pMT7-601 as previously described for production of pMT7-FMDV-1. The ligation mixture was used to transform *E. coli* strain JM83 and carbenicillin-resistant colonies selected. Two clones, designated pMT7-HIV and pMT7-HRV, were shown to contain the desired structure by restriction enzyme mapping and nucleotide sequence analysis.

For transcription, pMT7-HIV and pMT7-HRV, were linearised by digestion with EcoR1. Transcription using T7 RNA polymerase was carried out exactly as described for pMT7-601 and pBT7-123. The resulting transcripts were identical in size to natural virion RNA.

Demonstration of the Ability of PMT7-FMDV-1 and PMT7-HIV Transcripts to Replicate in Cowpea Protoplasts 10 μg samples of the in vitro transcripts from either pMT7-601, pMT7-FMDV-I or pMT7-HIV were mixed with 15 μg samples of transcripts from pBT7-123 and the mixtures used to electroporate $10^6$ cowpea mesophyll protoplasts. Samples were either taken immediately (0 hour) or after incubation of the protoplasts for 72 hour in the light at 25° C. Nucleic acids were extracted from one quarter of each sample and electrophoresed on a 1% formaldehyde-containing agarose gel as previously described. The nucleic acids were blotted on to Hybond N, cross-linked to the membrane by u.v. irradiation and probed for CPMV M RNA-specific sequences as previously described. In each case a strong hybridisation signal corresponding in position to M RNA could be detected in the 72 hour but not the 0 hour incubation samples, demonstrating that the transcripts from all four constructs can multiply in cowpea protoplasts.

The remaining three quarters of each protoplast sample was lysed as previously described and applied to electron microscope grids coated with anti-CPMV serum. The grids were then examined using a JEOL 1200 electron microscope. Large numbers of particles could be seen in the 72 hour samples of protoplasts electroporated with pMT7-601, pMT7-FMDV-I and pMT7-HIV transcripts. These results show that the modified coat proteins encoded by pMT7-FMDV-I and pMT7-HIV can assemble into virions.

Ability of PMT7-FMDV-I and pMT7-HIV Transcripts to Replicate in Whole Cowpea Plants To demonstrate the ability of transcripts from pMT7-FMDV-I and pMT7-HIV to replicate in whole cowpea plants in the presence of transcripts derived from pBT7-123, transcripts capped with GpppG were prepared as previously described. 6 groups, each consisting of 5, 10 day old, cowpeas, were inoculated with the transcripts using the method previously described. In each case, the amount of transcript refers to the amount applied to an individual leaf.

| | |
|---|---|
| Group 1. | Mock-inoculated with 50 mM Tris-phosphate, pH 8.0 |
| Group 2. | Inoculated with 1.5 μg of natural CPMV virion RNA |
| Group 3. | Inoculated with 5 μg each of pMT7-601 + pBT7-123 transcripts |
| Group 4. | Inoculated with 5 μg each of pMT7-FMDV-I + pBT7-123 transcripts |
| Group 5. | Inoculated with 5 μg each of pMT7-HIV + pBT7-123 transcripts |

Symptoms were scored on a daily basis and samples of leaf tissue from each plant were taken 11 days post-inoculation for "dot blot" analysis which was carried out as described previously. The rest of the leaf tissue from all the plants in groups 4 and 5 was harvested and frozen for future use.

Results

None of the plants in group 1 (mock-inoculated) developed any symptoms up to 11 days post infection (P.I.) and no CPMV-specific nucleic acids could be detected in the leaf tissue by "dot blot" analysis. This shows that no accidental infection of the cowpea plants with CPMV had occurred during the experiment. All plants in groups 2 and 3 (inoculated with either virion RNA or a mixture of pMT7-601 and pBT7-123 transcripts) showed strong symptoms on both the inoculated and systemic leaves by 7 days P.I. "Dot blot" analysis of leaf tissue showed the presence of large amounts of virus-specific RNA in both the inoculated and systemic leaves of all plants. This confirms that the plants used in the experiment were fully susceptible to infection with CPMV using either virion RNA or a mixture of wild-type transcripts.

By 11 days P.I. the inoculated leaves of all the plants in group 4 (inoculated with pMT7-FMDV-1 transcripts) developed a mottled appearance distinct from that normally associated with a wild-type virus infection. This result shows that the transcripts from pMT7-FMDV-I can multiply and spread from cell-to-cell in whole cowpea plants.

4 out of 5 of the plants in group 5 (inoculated with pMT7-HIV transcripts) developed symptoms on their systemic leaves by 11 days P.I. "Dot blot analysis showed that plants showing symptoms had substantial quantities of virus-specific sequences in both the inoculated and systemic leaves. This result shows that transcripts from pMT7-HIV can multiply and spread within whole cowpea plants.

Further Investigation of the Results Obtained with PMT7-FMDV-I and PMT7-HIV pMT7-FMDV-1: To demonstrate that modified viral capsid proteins were synthesised in the inoculated leaves of the group 4 plants, samples of the frozen leaf tissue were finely ground and extracted with IX Laemmli sample buffer.

Figure 11:
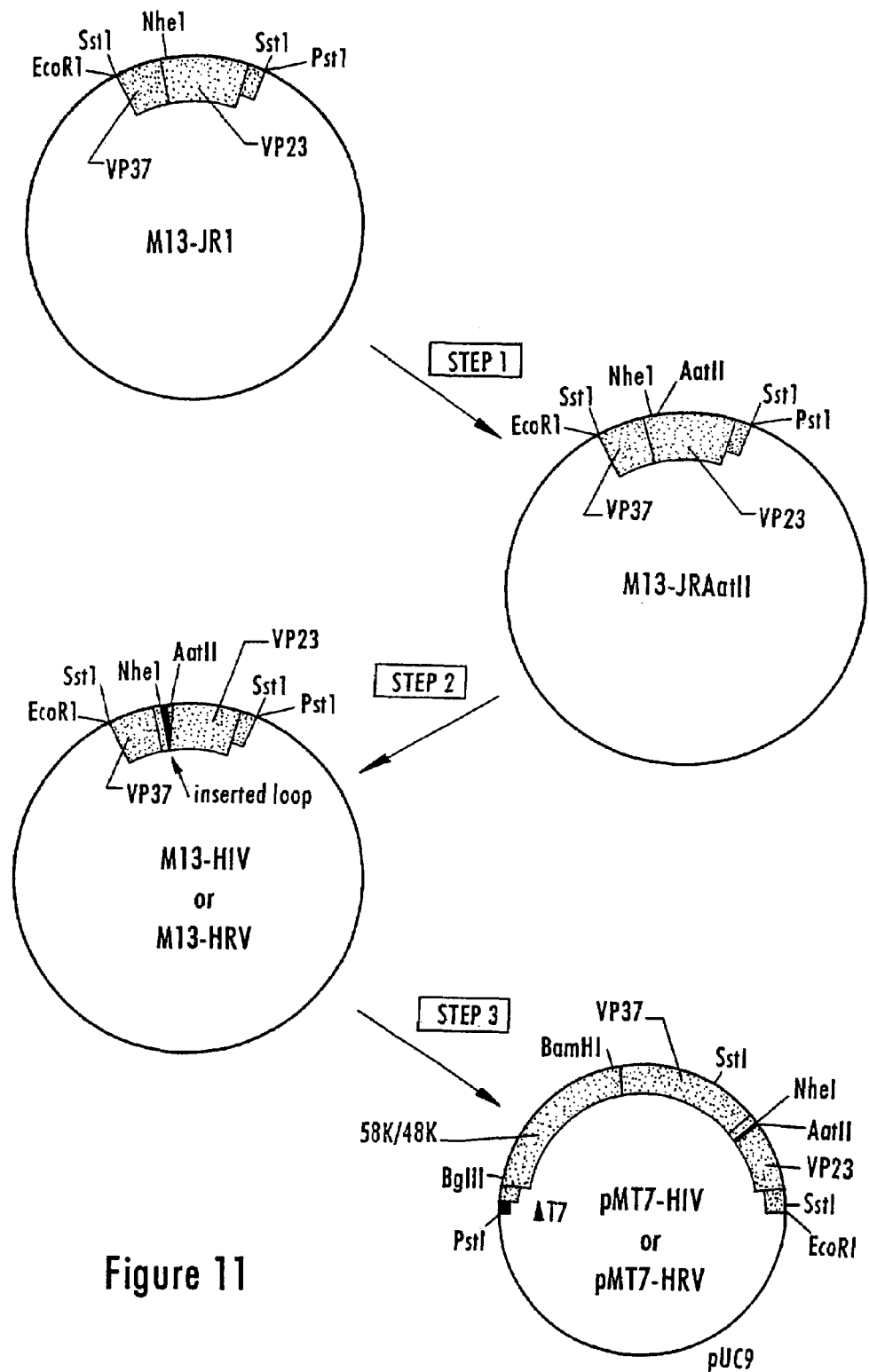
Figure 12:
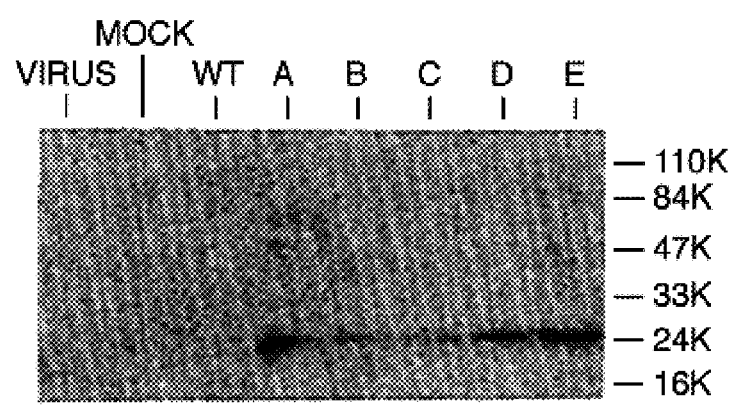

The extracts were electrophoresed on 15% polyacrylamide-SDS gels and the proteins transferred to nitrocellulose membranes using a Biorad semi-dry transfer cell. The membranes were probed either with serum raised against whole CPMV virus particles or with a serum raised against the synthetic oligopeptide, VPNLRGDLQVLAQKVARTLP (CG) (SEQ ID NO:22), corresponding to residues 141–160 of VP1 of FMDV strain $O_1$. This sequence corresponds to the epitope which was inserted into VP23 in pMT7-FMDV. Both antisera were raised in rabbits. Western blot analysis was carried out using alkaline phosphatase-conjugated goat anti-rabbit IgG as the second antibody. The protein extracts of all five group 4 plants were found to react with the anti-CPMV serum indicating that the virus coat proteins were synthesised in the inoculated leaves of the group 4 plants. When similar blots were probed with the anti-FMDV oligopeptide serum, a single band lit up in the extracts from each of the group 4 plants (FIG. 11). This band migrated with an apparent molecular weight of 24 kDa, which is exactly the size expected for VP23 carrying the FMDV loop. No product of similar size could be seen when extracts from mock-inoculated or wild-type CPMV-inoculated leaves were analysed (FIG. 11). Likewise, purified wild-type CPMV coat proteins did react with the FMDV-specific antiserum. Furthermore, pre-treatment of the anti-FMDV serum with the peptide which was used to raise it, abolished the reaction with the extracts from the group 4 plants demonstrating the specificity of the immunological reaction. These results demonstrate that the inoculated leaves of the group 4 plants contained CPMV coat proteins harbouring the FMDV loop.

pMT7-HIV: As discussed above, the "dot blot" analysis of both the inoculated and systemic leaves from the Group 5 plants indicated that transcripts from pMT7-HIV can multiply and spread in whole plants. The levels of signal obtained and the fact that the infection went systemic show that the progeny RNA is encapsidated. To prove that the HIV-specific insert was retained in the progeny RNA, "dot blots" of extracts from the group 5 plants were probed with a HIV-insert specific probe. This was made by "oligo-labelling" the positive sense oligonucleotide used in the construction of pMT7-HIV (see FIG. 9). The results obtained showed the presence of the HIV sequence in extracts of the inoculated leaves of the four plants which showed symptoms.

Extension of Results with CPMV Harbouring the FMDV Epitope

To extend the previous findings obtained with transcripts derived from pMT7-FMDV-I, five groups of five cowpea plants were inoculated with capped transcripts, prepared as previously described, as follows:

| | |
|---|---|
| Group 1: | Mock-inoculated with 50 mM Tris-phosphate, pH 8.0 |
| Group 2: | Inoculated with 0.5 µg of natural CPMV virion RNA |
| Group 3: | Inoculated with 5 µg GppppG capped pMT7-601 + pBT7-123 transcripts |
| Group 4: | Inoculated with 5 µg GppppG capped pMT7-FMDV-I + pBT7-123 transcripts |

Symptoms were scored on a daily basis. 13 days post-inoculation triplicate leaf disk samples were taken from one inoculated and one trifoliate leaf of each plant. The samples were treated as follows:

Sample 1 (Crude homogenate): Homogenised in 0.4 mls 10 mM sodium phosphate buffer, pH7.0, centrifuged and the supernatant recovered.

Sample 2 (RNA extract): Frozen in liquid nitrogen, finely ground and the nucleic acids extracted with phenol/chloroform. After ethanol precipitation, the nucleic acids were finally resuspended in 0.1 mls of water.

Sample 3 (Protein extract): Frozen in liquid nitrogen, finely ground and the powder dissolved in 0.1 ml 1× Laemmli sample buffer.

"Dot blots" were prepared from 5 µl aliquots of samples 1 and 2 and were probed with either a probe specific for nucleotides 482–2211 of CPMV M RNA (CPMV-specific probe), prepared as described previously, or with a probe specific for FMDV-specific insert. The latter was prepared by "oligo-labelling" the positive sense oligonucleotide shown in FIG. 5. Western blots were prepared from aliquots of sample 3 and probed for FMDV-specific epitopes as described previously. ISEM was carried out on aliquots of sample 1.

Results

No symptoms developed on any of the group 1 (mock inoculated) plants. Dot blots of crude homogenates or RNA extracts revealed no CPMV-specific or FMDV-specific sequences were present in extracts from either the inoculated or trifoliate leaves. ISEM of the crude homogenates using electron microscopy grids coated with anti CPMV serum showed no virus particles were present. Western blot analysis of the protein extracts using the FMDV-specific serum showed an absence of any FMDV epitopes. These results provide the negative control for the rest of the experiment.

Symptoms developed on both the inoculated and trifoliate leaves of all group 2 (virion RNA-inoculated) and group 3 (pMT7-601+pBT7-123)-inoculated plants by 7 days P.I. By 11 days PI the lesions on the primary leaves had expanded to a diameter of 2–3 mm. Dot blots of both the crude homogenates and RNA extracts revealed the presence of CPMV-specific but not FMDV-specific sequences. ISEM using grids coated with anti-CPMV serum revealed the presence of copious numbers of CPMV particles in crude homogenates from both the inoculated and trifoliate leaves. Western blot analysis of the protein extracts showed an absence of any FMDV epitopes.

Small lesions (approximately 1 mm in diameter) developed on the inoculated leaves of the group 4 (pMT7-FMDV-I+pBT7-123)-inoculated plants by 11 days P.I. Dot blots of the RNA extracted from the leaves (sample 2) showed the presence of both CPMV- and FMDV-specific sequences in the inoculated of 3 out of the 5 group 4 plants. ISEM using grids coated with anti-CPMV serum revealed the presence of CPMV-like virus particles in the crude homogenates from the inoculated leaves of 4 out of the 5 group 4 plants. Western blotting of the protein extracts (sample 3) revealed the presence of the FMDV epitope on the small coat protein in extracts from all group 4 plants. These results confirm that transcripts from pMT7-FMDV-I can multiply in whole cowpea plants and show that virus particles are produced in such plants.

Preparation of Virus from Transcript-Inoculated Plants

To isolate virus particles from pMT7-FMDV-I-infected leaf tissue the following method was developed:

22 grams of primary cowpea leaves which had been inoculated with 5 µg each of pBT7-123 and pMT7-FMDV transcripts were harvested 16 days post-inoculation. The leaves were homogenised in 2 volumes (approximately 50 mls) of 0.1M sodium phosphate, pH 7.0 at 4° C. The sap was filtered through two layers of muslin, centrifuged at 15,000 g for 15 minutes and the supernatant retained. The pellet was re-extracted with a few mls of 0.1M sodium phosphate buffer pH 7.0, re-centrifuged. The supernatants were combined and centrifuged in a Beckman type 30 rotor at 27,000 rpm for 4 hours at 4° C. The resulting pellet was resuspended overnight at 4° C. in 3.5 mls of 0.1M sodium phosphate, pH 7.0 and subsequently centrifuged in an Eppendorf centrifuge for 10 minutes. The supernatant was taken and made up to 4 mls with 0.1M sodium phosphate pH 7.0 and 1 ml of a solution containing 1M NaCl, 20% PEG 6000 was added and the mixture incubated for 2 hours at room temperature. The resulting precipitate was collected by centrifugation in an Eppendorf centrifuge for 10 minutes, resuspended in 0.25 mls of 10 mM sodium phosphate, pH 7.0 and the solution clarified by re-centrifugation in an Eppendorf centrifuge for 10 minutes. The supernatant, which contains the virus particles, was then removed and stored at 4° C. It was estimated spectrophotometrically that the virus concentration in the final suspension was approximately 1.5 mg/ml. Western blot analysis of the virus using FMDV-specific antiserum revealed the presence of FMDV antigen associated with the small coat protein subunit of the chimaeric virus particles.

Passaging Modified RNA

In order to produce large quantities of chimaeric virus as efficiently as possible, RNA extracted from transcript-inoculated leaves was passaged in plants. 5 μl samples of the RNA extract from a pMT7-FMDV-I-inoculated leaf were diluted to 50 μl with Tris-phosphate pH 8.0 and were inoculated on to the primary leaves of a batch of 5 cowpea plants. All the plants developed symptoms typical of a CPMV infection and at 23 days PI the primary leaves from the plants were harvested. The leaves were homogenised in 0.1 M sodium phosphate buffer and virus extracted as described above except that the initial high speed pelleting step was omitted. A total of 3.0 mgs of virus at a final concentration of 0.5 mg/ml in 10 mM sodium phosphate pH7.0 was isolated in this way. This preparation was finally concentrated in a Centriprep concentrator (Amicon) to a final concentration of 1.4 mg/ml and has been designated P1.

Samples of P1 were examined by electrophoresis on SDS gels and Coomassie Blue staining and shown to contain the expected pattern of coat proteins. Western blot analysis using anti-FMDV serum showed the small coat proteins contained the FMDV loop. RNA extracted from the virus particles was of the expected size for M and B RNA of CPMV. This demonstrates that chimaeric virus can be produced by passaging the RNA derived from transcript-inoculated leaves.

An experimental vaccine was prepared from virus preparation P1 by dispersion in sterile phosphate buffered saline (PBS) at a final concentration of 1 mg/ml. Guinea pigs were injected with 40 μg of the P1 vaccine on days 0 and 28. Preliminary results indicate that the animals produce antibodies against the FMDV loop, a response not seen when wild-type virus is injected.

REFERENCES

Ahlquist, P., and Janda, M. (1984). Mol. Cell. Biol. 4, 2876–2882.

Biggin, M. D., Gibson, T. J. and Hong, G. F. (1983). Proc. Natl. Acad. Sci. USA 80, 3963–3965.

Birnboim, H. C. and Doly, J. (1979). Nucleic acids Res. 7, 1513–1523.

Chanh, T. C., Dreesman, G. R., Kanda, P., Linette, G. P., Sparrow, J. T., Ho, D. D. and Kennedy, R. C., (1986). EMBO J. 5, 3065–3071.

Daigleish, A. G., Chanh, T. C., Kennedy, R. C., Kanda, P., Clapham, P. R. and Weiss, R. A. (1988). Virology 165, 209–215.

De Varennes, A. and Maule, A. J. (1985). Virology 144, 495–501.

Dessens, J. T. and Lomonossoff, G. P. (1991). Virology 184, 738–746.

Feinberg, A. P. and Vogelstein, B. (1983). Analytical Biochem. 132, 6–13.

Goldbach, R., Rezelman, G. and van Kammen, A. (1980). Nature 286, 297–300.

Holness, C. L. (1989). PhD Thesis, University of Warwick.

Holness, C. L., Lomonossoff, G. P., Evans, D. and Maule, A. J. (1989). Virology 172, 311–320.

Kennedy, R. C., Henkel, R. D., Pauletti, D., Allan, J. S., Lee, T. H., Essex, M. and Dreesman, G. R. (1986). Science 231, 1556–1559.

Kunkel, T. A. (1985). Proc. Nat. Acad. Sci. USA 82, 488–492.

Laemmli, U. K. (1970). Nature 227, 680–685.

Lehrach, H., Diamond, D., Wozney, J. M. and Boedtker, H. (1977). Biochemistry 16, 4743–4751.

Lomonossoff, G. P. and Shanks, M. (1983). EMBO J. 2, 2253–2258.

Lomonossoff, G. P., Shanks, M., Matthes, H. D., Singh, M. and Gait, M. J. (1982). Nucleic Acids Research 10, 4861–4872.

Maniatis, T., Fritsch, E. F. and Sambrooke, J. (1982). Molecular Cloning. A Laboratory Manual. Cold Spring Harbor Laboratory.

Pelham, H. R. B. and Jackson, R. J. (1976). Eur. J. Biochem. 67, 247–256.

Sanger, F., Coulson, A. R., Barrell, B. G., Smith, A. J. H. and Roe, B. A. (1980). J. Mol. Biol. 143, 161–178.

Shanks, M., Stanley, J. and Lomonossoff, G. P. (1986). Virology 155, 697–706.

van Wezenbeek, P., Verver, J., Harmsen, J., Vos, P., and van Kammen, A. (1983). EMBO J. 2, 941–946.

Ziegler-Graff, V., Bouzoubaa, S., Jupin, I., Guilley, H., Jonard, G. and Richards, K. (1988). J. Gen. Virol. 69, 2347–2357.

The invention claimed is:

1. A plant infected with a modified plant virus, said modified plant virus comprising modified plant viral nucleic acid and expressed plant viral coat protein, said modified plant viral nucleic acid comprising a nucleotide sequence coding for a foreign peptide from an animal virus inserted into said plant viral nucleic acid in a region that codes for an exposed part of an expressed native portion of the plant viral coat protein, said inserted nucleotide sequence being an addition to the existing native functional plant viral nucleic acid, said foreign peptide being greater than five amino acids in length, wherein said plant contains assembled modified plant virus resulting from the assembly of said modified plant virus, wherein said modified plant virus is a modified comovirus.

2. The plant of claim 1, wherein said nucleotide sequence coding for a foreign peptide is from Foot and Mouth disease virus.

3. The plant of claim 1, wherein said nucleotide sequence coding for a foreign peptide is from human immune deficiency virus.

4. The plant of claim 1, wherein said nucleotide sequence coding for a foreign peptide is from human rhinovirus.

* * * * *

SEQUENCE LISTING

```
<160> NUMBER OF SEQ ID NOS: 22

<210> SEQ ID NO 1
<211> LENGTH: 120
```

```
<212> TYPE: DNA
<213> ORGANISM: Cowpea mosaic virus
<220> FEATURE:
<221> NAME/KEY: CDS
<222> LOCATION: (1)..(120)
<223> OTHER INFORMATION:

<400> SEQUENCE: 1 gga cct gtt tgt gct gaa gcc tca gat gtg tat agc cca tgt atg ata        48
Gly Pro Val Cys Ala Glu Ala Ser Asp Val Tyr Ser Pro Cys Met Ile
1               5                   10                  15 gct agc act cct cct gct cca ttt tca gac gtt aca gca gta act ttt        96
Ala Ser Thr Pro Pro Ala Pro Phe Ser Asp Val Thr Ala Val Thr Phe
            20                  25                  30 gac tta atc aac ggc aaa ata act                                       120
Asp Leu Ile Asn Gly Lys Ile Thr
        35                  40

<210> SEQ ID NO 2
<211> LENGTH: 40
<212> TYPE: PRT
<213> ORGANISM: Cowpea mosaic virus

<400> SEQUENCE: 2

Gly Pro Val Cys Ala Glu Ala Ser Asp Val Tyr Ser Pro Cys Met Ile
1               5                   10                  15

Ala Ser Thr Pro Pro Ala Pro Phe Ser Asp Val Thr Ala Val Thr Phe
            20                  25                  30

Asp Leu Ile Asn Gly Lys Ile Thr
        35                  40

<210> SEQ ID NO 3
<211> LENGTH: 81
<212> TYPE: DNA
<213> ORGANISM: Foot-and-mouth disease virus
<220> FEATURE:
<221> NAME/KEY: CDS
<222> LOCATION: (3)..(80)
<223> OTHER INFORMATION:

<400> SEQUENCE: 3 ct agc act tat agt aga aat gct gtt cct aat ttg aga gga gat ctt         47
   Ser Thr Tyr Ser Arg Asn Ala Val Pro Asn Leu Arg Gly Asp Leu
   1               5                   10                  15 caa gtt ttg gct caa aag gtt gct cgg act ctt c                          81
Gln Val Leu Ala Gln Lys Val Ala Arg Thr Leu
                20                  25

<210> SEQ ID NO 4
<211> LENGTH: 26
<212> TYPE: PRT
<213> ORGANISM: Foot-and-mouth disease virus

<400> SEQUENCE: 4

Ser Thr Tyr Ser Arg Asn Ala Val Pro Asn Leu Arg Gly Asp Leu Gln
1               5                   10                  15

Val Leu Ala Gln Lys Val Ala Arg Thr Leu
            20                  25

<210> SEQ ID NO 5
<211> LENGTH: 156
<212> TYPE: DNA
<213> ORGANISM: Foot-and-mouth disease virus
<220> FEATURE:
<221> NAME/KEY: CDS
```

```
<222> LOCATION: (1)..(156)
<223> OTHER INFORMATION:

<400> SEQUENCE: 5 gga cct gtt tgt gct gaa gcc tca gat gtg tat agc cca tgt atg ata        48
Gly Pro Val Cys Ala Glu Ala Ser Asp Val Tyr Ser Pro Cys Met Ile
1               5                   10                  15 gct agc act tat agt aga aat gct gtt cct aat ttg aga gga gat ctt        96
Ala Ser Thr Tyr Ser Arg Asn Ala Val Pro Asn Leu Arg Gly Asp Leu
            20                  25                  30 caa gtt ttg gct caa aag gtt gct cgg act ctt cct agc act cct cct       144
Gln Val Leu Ala Gln Lys Val Ala Arg Thr Leu Pro Ser Thr Pro Pro
        35                  40                  45 gct cca ttt tca                                                       156
Ala Pro Phe Ser
    50

<210> SEQ ID NO 6
<211> LENGTH: 52
<212> TYPE: PRT
<213> ORGANISM: Foot-and-mouth disease virus

<400> SEQUENCE: 6

Gly Pro Val Cys Ala Glu Ala Ser Asp Val Tyr Ser Pro Cys Met Ile
1               5                   10                  15

Ala Ser Thr Tyr Ser Arg Asn Ala Val Pro Asn Leu Arg Gly Asp Leu
            20                  25                  30

Gln Val Leu Ala Gln Lys Val Ala Arg Thr Leu Pro Ser Thr Pro Pro
        35                  40                  45

Ala Pro Phe Ser
    50

<210> SEQ ID NO 7
<211> LENGTH: 69
<212> TYPE: DNA
<213> ORGANISM: Cowpea mosaic virus
<220> FEATURE:
<221> NAME/KEY: CDS
<222> LOCATION: (1)..(69)
<223> OTHER INFORMATION:

<400> SEQUENCE: 7 cca tgt atg ata gct agc act cct cct gct cca ttt tca gac gtt aca        48
Pro Cys Met Ile Ala Ser Thr Pro Pro Ala Pro Phe Ser Asp Val Thr
1               5                   10                  15 gca gta act ttt gac tta atc                                            69
Ala Val Thr Phe Asp Leu Ile
            20

<210> SEQ ID NO 8
<211> LENGTH: 23
<212> TYPE: PRT
<213> ORGANISM: Cowpea mosaic virus

<400> SEQUENCE: 8

Pro Cys Met Ile Ala Ser Thr Pro Pro Ala Pro Phe Ser Asp Val Thr
1               5                   10                  15

Ala Val Thr Phe Asp Leu Ile
            20

<210> SEQ ID NO 9
<211> LENGTH: 69
<212> TYPE: DNA
```

```
<213> ORGANISM: Cowpea mosaic virus
<220> FEATURE:
<221> NAME/KEY: CDS
<222> LOCATION: (1)..(69)
<223> OTHER INFORMATION:

<400> SEQUENCE: 9 cca tgt atg ata gct agc act cct cct gct cca ttt tca gac gtc aca        48
Pro Cys Met Ile Ala Ser Thr Pro Pro Ala Pro Phe Ser Asp Val Thr
1               5                  10                  15 gca gta act ttt gac tta atc                                            69
Ala Val Thr Phe Asp Leu Ile
            20

<210> SEQ ID NO 10
<211> LENGTH: 23
<212> TYPE: PRT
<213> ORGANISM: Cowpea mosaic virus

<400> SEQUENCE: 10

Pro Cys Met Ile Ala Ser Thr Pro Pro Ala Pro Phe Ser Asp Val Thr
1               5                  10                  15

Ala Val Thr Phe Asp Leu Ile
            20

<210> SEQ ID NO 11
<211> LENGTH: 67
<212> TYPE: DNA
<213> ORGANISM: Human immunodeficiency virus
<220> FEATURE:
<221> NAME/KEY: CDS
<222> LOCATION: (3)..(65)
<223> OTHER INFORMATION:

<400> SEQUENCE: 11 ct agc act gac cgc cct gag ggc atc gag gaa gag ggc ggt gag cgc         47
   Ser Thr Asp Arg Pro Glu Gly Ile Glu Glu Glu Gly Gly Glu Arg
   1               5                  10                  15 gat cgt gat cgt tcg gac gt                                             67
Asp Arg Asp Arg Ser Asp
            20

<210> SEQ ID NO 12
<211> LENGTH: 21
<212> TYPE: PRT
<213> ORGANISM: Human immunodeficiency virus

<400> SEQUENCE: 12

Ser Thr Asp Arg Pro Glu Gly Ile Glu Glu Glu Gly Gly Glu Arg Asp
1               5                  10                  15

Arg Asp Arg Ser Asp
            20

<210> SEQ ID NO 13
<211> LENGTH: 141
<212> TYPE: DNA
<213> ORGANISM: Human immunodeficiency virus
<220> FEATURE:
<221> NAME/KEY: CDS
<222> LOCATION: (1)..(141)
<223> OTHER INFORMATION:

<400> SEQUENCE: 13 gga cct gtt tgt gct gaa gcc tca gat gtg tat agc cca tgt atg ata        48
Gly Pro Val Cys Ala Glu Ala Ser Asp Val Tyr Ser Pro Cys Met Ile
1               5                  10                  15
```

```
gct agc act gac cgc cct gag ggc atc gag gaa gag ggc ggt gag cgc        96
Ala Ser Thr Asp Arg Pro Glu Gly Ile Glu Glu Glu Gly Gly Glu Arg
            20                  25                  30 gat cgt gat cgt tcg gac gtc aca gca gta act ttt gac tta atc          141
Asp Arg Asp Arg Ser Asp Val Thr Ala Val Thr Phe Asp Leu Ile
        35                  40                  45
```

<210> SEQ ID NO 14
<211> LENGTH: 47
<212> TYPE: PRT
<213> ORGANISM: Human immunodeficiency virus

<400> SEQUENCE: 14

```
Gly Pro Val Cys Ala Glu Ala Ser Asp Val Tyr Ser Pro Cys Met Ile
1               5                   10                  15

Ala Ser Thr Asp Arg Pro Glu Gly Ile Glu Glu Glu Gly Gly Glu Arg
            20                  25                  30

Asp Arg Asp Arg Ser Asp Val Thr Ala Val Thr Phe Asp Leu Ile
        35                  40                  45
```

<210> SEQ ID NO 15
<211> LENGTH: 52
<212> TYPE: DNA
<213> ORGANISM: Human rhinovirus
<220> FEATURE:
<221> NAME/KEY: CDS
<222> LOCATION: (3)..(50)
<223> OTHER INFORMATION:

<400> SEQUENCE: 15

```
ct agc act cct gct act gga atc gat aat cat aga gaa gct aaa ttg        47
   Ser Thr Pro Ala Thr Gly Ile Asp Asn His Arg Glu Ala Lys Leu
   1               5                   10                  15 gac gt                                                                52
Asp
```

<210> SEQ ID NO 16
<211> LENGTH: 16
<212> TYPE: PRT
<213> ORGANISM: Human rhinovirus

<400> SEQUENCE: 16

```
Ser Thr Pro Ala Thr Gly Ile Asp Asn His Arg Glu Ala Lys Leu Asp
1               5                   10                  15
```

<210> SEQ ID NO 17
<211> LENGTH: 126
<212> TYPE: DNA
<213> ORGANISM: Human rhinovirus
<220> FEATURE:
<221> NAME/KEY: CDS
<222> LOCATION: (1)..(126)
<223> OTHER INFORMATION:

<400> SEQUENCE: 17

```
gga cct gtt tgt gct gaa gcc tca gat gtg tat agc cca tgt atg ata        48
Gly Pro Val Cys Ala Glu Ala Ser Asp Val Tyr Ser Pro Cys Met Ile
1               5                   10                  15 gct agc act cct gct act gga atc gat aat cat aga gaa gct aaa ttg        96
Ala Ser Thr Pro Ala Thr Gly Ile Asp Asn His Arg Glu Ala Lys Leu
            20                  25                  30 gac gtc aca gca gta act ttt gac tta atc                              126
Asp Val Thr Ala Val Thr Phe Asp Leu Ile
        35                  40
```

-continued

<210> SEQ ID NO 18
<211> LENGTH: 42
<212> TYPE: PRT
<213> ORGANISM: Human rhinovirus

<400> SEQUENCE: 18

```
Gly Pro Val Cys Ala Glu Ala Ser Asp Val Tyr Ser Pro Cys Met Ile
1               5                   10                  15

Ala Ser Thr Pro Ala Thr Gly Ile Asp Asn His Arg Glu Ala Lys Leu
            20                  25                  30

Asp Val Thr Ala Val Thr Phe Asp Leu Ile
        35                  40
```

<210> SEQ ID NO 19
<211> LENGTH: 18
<212> TYPE: DNA
<213> ORGANISM: Escherichia coli

<400> SEQUENCE: 19

```
agttactgct gtaacgtc                                                18
```

<210> SEQ ID NO 20
<211> LENGTH: 43
<212> TYPE: DNA
<213> ORGANISM: Cowpea mosaic virus

<400> SEQUENCE: 20

```
ccctgcagta atacgactca ctatagtatt aaaatcttaa tag                    43
```

<210> SEQ ID NO 21
<211> LENGTH: 19
<212> TYPE: DNA
<213> ORGANISM: Escherichia coli

<400> SEQUENCE: 21

```
ctgctgtgac gtctgaaaa                                               19
```

<210> SEQ ID NO 22
<211> LENGTH: 22
<212> TYPE: PRT
<213> ORGANISM: Cowpea mosaic virus

<400> SEQUENCE: 22

```
Val Pro Asn Leu Arg Gly Asp Leu Gln Val Leu Ala Gln Lys Val Ala
1               5                   10                  15

Arg Thr Leu Pro Cys Gly
            20
```